United States Patent [19]
Hasegawa et al.

[11] Patent Number: 6,051,407
[45] Date of Patent: Apr. 18, 2000

[54] CELLULOSE SYNTHASE GENE

[75] Inventors: Osamu Hasegawa; Satoshi Aotsuka, both of Tokyo; Takahisa Hayashi, 544, Kyodai-shukusha, Gokasho, Uji, Kyoto, 611; Yuri Ihara, Osaka, all of Japan

[73] Assignees: Nisshinbo Industries, Inc.; Takahisa Hayashi, both of Japan

[21] Appl. No.: 09/050,392

[22] Filed: Mar. 30, 1998

[30] Foreign Application Priority Data

Apr. 1, 1997 [JP] Japan ................................. 9-083133

[51] Int. Cl.⁷ ............................. C12P 19/04; C12N 9/12; C12N 15/54
[52] U.S. Cl. ...................... 435/101; 435/194; 435/320.1; 435/252.3; 536/23.2
[58] Field of Search ..................... 435/101, 194, 435/252.3, 320.1; 536/23.2

[56] References Cited

U.S. PATENT DOCUMENTS 5,268,274 12/1993 Ben-Bassat et al. .................... 435/69.1

FOREIGN PATENT DOCUMENTS

WO 91 13988 9/1991 WIPO .
WO 98 00549 1/1998 WIPO .
WO 98 18949 5/1998 WIPO .

OTHER PUBLICATIONS

GenBank Database Accession U58283 "Gossypium hirsutum cellulose synthase (celA1) mRNA, complete cds" Submitted by Pear et al, Dec. 5, 1996.
GenBank Database Accession U58284 "Gossypium hirsutum cellulose synthase (celA1) mRNA, complete cds" Submitted by Pear et al, Dec. 5, 1996.
Pear, J. R. et al.; "*Higher Plants Contain Homologs of the Bacterial CelA Genes Encoding the Catalytic Subunit of Cellulose Synthase*", Proc. Natl.Acad.Sci.USA, vol. 93, Oct. 1996, pp. 12637–12642.
Li, L., et al.; "*B–Glucan Synthesis in the 1–4 Cotton Fiber*", Plant Physiology, vol. 101, No. 4, 1993, pp. 1149–1156.

*Primary Examiner*—Ponnathapu Achutamurthy
*Assistant Examiner*—Bradley S. Mayhew
*Attorney, Agent, or Firm*—Jones & Askew, LLP

[57] ABSTRACT mRNA was extracted at the stage for cotton plant fibrous cells to accumulate cellulose, and cDNA's complementary thereto were synthesized to construct a cDNA library. Clones of a number of 750 were arbitrarily selected from the library, and they were randomly subjected to sequencing. Those having homology to an amino acid sequence deduced from a gene of cellulose 4-β-glucosyltransferase (bcsA) of cellulose synthase operon of acetic acid bacterium were selected from obtained nucleotide sequences of the respective clones. Thus, DNA coding for cellulose synthase was obtained.

15 Claims, 3 Drawing Sheets

SEQ ID NO: 14

5'    A A T T C G G C A C G A G    3'
3'            G C C G T G C T C    5'  ---

```
              10         20         30         40         50         60
PcsA3-682    CCGACATTCGTGAAGGAGCGTCGAGCTATGAAGAGAGAATATGAAGAATTCAAGGTTAGG
(SEQ ID NO: 5)  ::::::::::::::::::::::::::::::::::::::::::::::::::::::::::::
PcsA3-3'     CCGACATTCGTGAAGGAGCGTCGAGCTATGAAGAGAGAATATGAAGAATTCAAGGTTAGG
(SEQ ID NO: 9)  20         30         40         50         60         70
              70         80         90        100        110        120
PcsA3-682    ATAAATGCACTTGTAGCCAAAGCCCAAAAGGTTCCTCCAGAAGGGTGGATCATGCAAGAT
              ::::::::::::::::::::::::::::::::::::::::::::::::::::::::::::
PcsA3-3'     ATAAATGCACTTGTAGCCAAAGCCCAAAAGGTTCCTCCAGAAGGGTGGATCATGCAAGAT
              80         90        100        110        120        130
             130        140        150        160        170        180
PcsA3-682    GGGACACCATGGCCAGGAAACAATACTAAAGATCACCCTGGTATGATTCAAGTATTTCTC
              ::::::::::::::::::::::::::::::::::::::::::::::::::::::::::::
PcsA3-3'     GGGACACCATGGCCAGGAAACAATACTAAAGATCACCCTGGTATGATTCAAGTATTTCTC
             140        150        160        170        180        190
             190        200        210        220        230        240
PcsA3-682    GGTCAAAGTGGAGGCCATGATACCGAAGGAAATGAGCTTCCTCGTCTCGTCTATGTATCT
              ::::::::::::::::::::::::::::::::::::::::::::::::::::::::::::
PcsA3-3'     GGTCAAAGTGGAGGCCATGATACCGAAGGAAATGAGCTTCCTCGTCTCGTCTATGTATCT
             200        210        220        230        240        250
             250        260        270        280        290        300
PcsA3-682    CGAGAGAAAAGGCCTGGTTTCTTGCATCACAAGAAAGCTGGTGCCATGAACGCCCTTGTT
              ::::::::::::*:::::::::::::::::::::::::::::::::::::::::::::::
PcsA3-3'     CGAGAGAAAAGGCCAGGTTTCTTGCATCACAAGAAAGCTGGTGCCATGAACGCCCTTGTT
             260        270        280        290        300        310
             310        320        330        340        350        360
PcsA3-682    CGGGTCTCGGGGGTGCTCACAAATGCTCCTTTTATGTTGAACTTGGATTGTGACCATTAT
              ::*:::::::::::*:::::::::::::::::::::::::::::::::::::::*:::
PcsA3-3'     CGTGTCTCGGGGGTGCTTACAAATGCTCCTTTTATGTTGAACTTGGATTGTGACCACTAT
             320        330        340        350        360        370
             370        380        390        400        410        420
PcsA3-682    TTAAATAACAGCAAGGCTGTAAGAGAGGCTATGTGTTTCTTGATGGACCCTCAAATTGGA
              ::::::::::::::::::::::::::::::::::::::::::::::::::::::::::::
PcsA3-3'     TTAAATAACAGCAAGGCTGTAAGAGAGGCTATGTGTTTCTTGATGGACCCTCAAATTGGA
             380        390        400        410        420        430
             430        440        450        460        470        480
PcsA3-682    AGAAAGGTTTGCTATGTCCAATTCCCTCAACGTTTCGATGGTATTGATAGACATGATCGA
              ::::::::::::::::::::::::::::::::::::::::::::::::::::::::::::
PcsA3-3'     AGAAAGGTTTGCTATGTCCAATTCCCTCAACGTTTCGATGGTATTGATAGACATGATCGA
             440        450        460        470        480        490
             490        500        510        520        530        540
PcsA3-682    TATGCCAATCGGAACACAGTTTTCTTTGATATTAACATGAAAGGTCTAGATGGTATACAA
              ::::::::::::::::::::::::::::::::::::::::::::::::::::::::::::
PcsA3-3'     TATGCCAATCGGAACACAGTTTTCTTTGATATTAACATGAAAGGTCTAGATGGTATACAA
             500        510        520        530        540        550
```

FIG. 3

```
            550        560        570        580        590        600
PcsA3-682   GGCCCTGTATATGTCGGCACGGGGTGTGTTTTCAGAAGGCAAGCTCTTTATGGTTATGAA
(SEQ ID NO: 5)
            ::::::::::::::::::::::::::::::::::::::::::::::::::::::::::::
PcsA3-3'    GGCCCTGTATATGTCGGCACGGGGTGTGTTTTCAGAAGGCAAGCTCTTTATGGTTATGAA
(SEQ ID NO: 9)
                       560        570        580        590        600        610

610        620        630        640        650        660
PcsA3-682   CCTCCAAAGGGACCTAAGCGCCCGAAAATGGTAACCTGTGGTTGCTGCCCTTGTTTTGGA
            ::::::::::::::::::::::::::::::::::::::::::::::::*:::::::
PcsA3-3'    CCTCCAAAGGGACCTAAGCGCCCGAAAATGGTAACCTGTGGTTGCTGCCCTTGCTTTGGA
            620        630        640        650        660        670

670        680        690        700        710        720
PcsA3-682   CGCCGCAGAAAGGACAAAAAGCACTCTAAGGATGGTGGAAATGCAAATGGTCTAAGCCTA
            ::::::::::::::::::::::::::::::::::::::::::::::::::::::::::::
PcsA3-3'    CGCCGCAGAAAGGACAAAAAGCACTCTAAGGATGGTGGAAATGCAAATGGTCTAAGCCTA
            680        690        700        710        720        730

730        740        750        760        770        780
PcsA3-682   GAAGCAGCCAAAGATGACAAGGAGTTATTGATGTCCCACATGAACTTTGAAAAGAAATTT
            ::::::::*:::::::::::::::::::::::::::::::::::::::::::::::::::
PcsA3-3'    GAAGCAGCCGAAGATGACAAGGAGTTATTGATGTCCCACATGAACTTTGAAAAGAAATTT
            740        750        760        770        780        790

790        800        810        820        830        840
PcsA3-682   GGACAATCAGCCATTTTTGTAACTTCAACACTGATGGAACAAGGTGGTGTCCCTCCTTCT
            ::::::::::::::::::::::::::::::::::::::::::::::::::::::::::::
PcsA3-3'    GGACAATCAGCCATTTTTGTAACTTCAACACTGATGGAACAAGGTGGTGTCCCTCCTTCT
            800        810        820        830        840        850

850        860        870        880        890        900
PcsA3-682   TCAAGCCCCGCAGCTTTGCTCAAAGAAGCCATTCATGTAATTAGTTGTGGTTATGAAGAC
            ::::::::*:::::::::::::::::::::::::::::::::::::::::::::::::::
PcsA3-3'    TCAAGCCCTGCAGCTTTGCTCAAAGAAGCCATTCATGTAATTAGTTGTGGTTATGAAGAC
            860        870        880        890        900        910

910        920        930        940        950        960
PcsA3-682   AAAACAGAATGGGGAAGCGAGCTTGGCTGGATTTACGGCTCGATTACAGAAGATATCTTA
            :::::*::::::::::::::::::::::::::::::::::::::::::::::::::::::
PcsA3-3'    AAAACCGAATGGGGAAGCGAGCTTGGCTGGATTTACGGCTCGATTACAGAAGATATCTTA
            920        930        940        950        960        970

970        980
PcsA3-682   ACAGGATTCAAGATGCATTGCCGTGGAT
            :::::*::::::::::::::::::::::
PcsA3-3'    ACAGGTTTCAAGATGCATTGCCGTGGAT
            980        990        1000
```

FIG. 4

SEQUENCE LISTING

<160> NUMBER OF SEQ ID NOS: 24

<210> SEQ ID NO 1
<211> LENGTH: 3207
<212> TYPE: DNA
<213> ORGANISM: Gossypium hirsutum
<220> FEATURE:
<221> NAME/KEY: CDS
<222> LOCATION: (77)..(3001)

<400> SEQUENCE: 1

```
ggttagcata ttgtttgtag cattgggttt ttttctcaag gaagaagaag gagaaagata      60
agtaatgttt ttgaga atg atg gaa tct ggg gtt cct gtt tgc cac act tgt     112
               Met Met Glu Ser Gly Val Pro Val Cys His Thr Cys
                 1               5                  10 ggt gaa cat gtt ggg ttg aat gtt aat ggt gaa ccc ttt gtg gct tgc      160
Gly Glu His Val Gly Leu Asn Val Asn Gly Glu Pro Phe Val Ala Cys
         15                  20                  25 cat gaa tgt aat ttc cct att tgt aag agt tgt ttt gag tat gat ctt      208
His Glu Cys Asn Phe Pro Ile Cys Lys Ser Cys Phe Glu Tyr Asp Leu
     30                  35                  40 aag gaa gga caa aaa gct tgc ttg cgt tgt ggt att ccg tat gat gaa      256
Lys Glu Gly Gln Lys Ala Cys Leu Arg Cys Gly Ile Pro Tyr Asp Glu
 45                  50                  55                  60 aac ctg ttg gac gat gtc gag aag gcc acc ggc gat caa tcg aca atg      304
Asn Leu Leu Asp Asp Val Glu Lys Ala Thr Gly Asp Gln Ser Thr Met
                 65                  70                  75 gct gca cat ttg agc aag tct cag gat gtt gga att cat gca aga cat      352
Ala Ala His Leu Ser Lys Ser Gln Asp Val Gly Ile His Ala Arg His
         80                  85                  90 atc agc agt gtg tct aca ttg gat agt gaa atg act gaa gac aat ggg      400
Ile Ser Ser Val Ser Thr Leu Asp Ser Glu Met Thr Glu Asp Asn Gly
     95                 100                 105 aat ccg att tgg aag aac agg gtg gaa agt tgg aaa gaa aag aag aac      448
Asn Pro Ile Trp Lys Asn Arg Val Glu Ser Trp Lys Glu Lys Lys Asn
110                 115                 120 aag aag aag aag cct gca aca act aag gtt gaa aga gag gct gaa atc      496
Lys Lys Lys Lys Pro Ala Thr Thr Lys Val Glu Arg Glu Ala Glu Ile
125                 130                 135                 140 cca cct gag caa caa atg gaa gat aaa ccg gca ccg gat gct tcc cag      544
Pro Pro Glu Gln Gln Met Glu Asp Lys Pro Ala Pro Asp Ala Ser Gln
                145                 150                 155 ccc ctc tcg act ata att cca atc ccg aaa agc aga ctt gca cca tac      592
Pro Leu Ser Thr Ile Ile Pro Ile Pro Lys Ser Arg Leu Ala Pro Tyr
        160                 165                 170 cga acc gtg atc att atg cga ttg atc att ctc ggt ctt ttc cat          640
Arg Thr Val Ile Ile Met Arg Leu Ile Ile Leu Gly Leu Phe Phe His
    175                 180                 185 tat cga gta aca aac ccc gtt gac agt gct ttt gga ctg tgg ctc act      688
Tyr Arg Val Thr Asn Pro Val Asp Ser Ala Phe Gly Leu Trp Leu Thr
    190                 195                 200 tca gtc ata tgt gaa atc tgg ttt gct ttt tcc tgg gtg ttg gat cag      736
Ser Val Ile Cys Glu Ile Trp Phe Ala Phe Ser Trp Val Leu Asp Gln
205                 210                 215                 220 ttc cct aag tgg tat cct gtt aac agg gaa aca tac att gac aga ctg      784
```

-continued

```
                Phe Pro Lys Trp Tyr Pro Val Asn Arg Glu Thr Tyr Ile Asp Arg Leu
                                    225                 230                 235 tct gca aga tat gaa aga gaa ggt gaa cct aat gaa ctt gct gca gtt        832
Ser Ala Arg Tyr Glu Arg Glu Gly Glu Pro Asn Glu Leu Ala Ala Val
            240                 245                 250 gac ttc ttt gtg agt aca gtg gat cca ttg aaa gag cct cca ttg att        880
Asp Phe Phe Val Ser Thr Val Asp Pro Leu Lys Glu Pro Pro Leu Ile
        255                 260                 265 act gcc aat act gtg ctt tcc atc ctt gcc ttg gac tac ccg gta gat        928
Thr Ala Asn Thr Val Leu Ser Ile Leu Ala Leu Asp Tyr Pro Val Asp
    270                 275                 280 aag gtc tct tgt tat ata tct gat gat ggt gcg gcc atg ctg aca ttt        976
Lys Val Ser Cys Tyr Ile Ser Asp Asp Gly Ala Ala Met Leu Thr Phe
285                 290                 295                 300 gaa tct cta gta gaa aca gcc gac ttt gca aga aag tgg gtt cca ttc       1024
Glu Ser Leu Val Glu Thr Ala Asp Phe Ala Arg Lys Trp Val Pro Phe
                305                 310                 315 tgc aaa aaa ttt tcc att gaa cca cgg gca cct gag ttt tac ttc tca       1072
Cys Lys Lys Phe Ser Ile Glu Pro Arg Ala Pro Glu Phe Tyr Phe Ser
            320                 325                 330 cag aag att gat tac ttg aaa gat aaa gtg cag ccc tct ttt gta aaa       1120
Gln Lys Ile Asp Tyr Leu Lys Asp Lys Val Gln Pro Ser Phe Val Lys
        335                 340                 345 gaa cgt aga gct atg aaa aga gat tac gaa gag tac aaa att cga atc       1168
Glu Arg Arg Ala Met Lys Arg Asp Tyr Glu Glu Tyr Lys Ile Arg Ile
    350                 355                 360 aat gct tta gtt gca aag gct cag aaa aca cct gaa gaa gga tgg aca       1216
Asn Ala Leu Val Ala Lys Ala Gln Lys Thr Pro Glu Glu Gly Trp Thr
365                 370                 375                 380 atg caa gat gga act cct tgg ccg gga aat aac ccg cgt gat cac cct       1264
Met Gln Asp Gly Thr Pro Trp Pro Gly Asn Asn Pro Arg Asp His Pro
                385                 390                 395 ggc atg att cag gtt ttc ctt gga tat agc ggt gct cat gac atc gaa       1312
Gly Met Ile Gln Val Phe Leu Gly Tyr Ser Gly Ala His Asp Ile Glu
            400                 405                 410 gga aat gaa ctt ccc cga ctg gtt tac gtc tct aga gag aag aga cct       1360
Gly Asn Glu Leu Pro Arg Leu Val Tyr Val Ser Arg Glu Lys Arg Pro
        415                 420                 425 ggc tac caa cac cac aaa aag gct ggt gct gaa aat gct ttg gtt agg       1408
Gly Tyr Gln His His Lys Lys Ala Gly Ala Glu Asn Ala Leu Val Arg
    430                 435                 440 gtg tct gca gtt ctt aca aat gct ccc ttc atc ctc aat ctt gat tgt       1456
Val Ser Ala Val Leu Thr Asn Ala Pro Phe Ile Leu Asn Leu Asp Cys
445                 450                 455                 460 gac cac tat gtt aac aat agc aag gca gtt agg gag gca atg tgc ttc       1504
Asp His Tyr Val Asn Asn Ser Lys Ala Val Arg Glu Ala Met Cys Phe
                465                 470                 475 ttg atg gac cca caa gtc ggt cga gat gtc tgc tat gtg cag ttt cct       1552
Leu Met Asp Pro Gln Val Gly Arg Asp Val Cys Tyr Val Gln Phe Pro
            480                 485                 490 caa aga ttt gat ggc ata gat agg agt gat cga tat gcc aat cgg aac       1600
Gln Arg Phe Asp Gly Ile Asp Arg Ser Asp Arg Tyr Ala Asn Arg Asn
        495                 500                 505 aca gtt ttc ttt gat gtt aac atg aaa ggt ctt gat gga atc caa ggg       1648
Thr Val Phe Phe Asp Val Asn Met Lys Gly Leu Asp Gly Ile Gln Gly
    510                 515                 520 cct gtt tat gtg gga aca ggt tgt gtt ttc aat agg caa gca ctt tat       1696
Pro Val Tyr Val Gly Thr Gly Cys Val Phe Asn Arg Gln Ala Leu Tyr
525                 530                 535                 540
```

| | |
|---|---|
| ggc tat ggt cca cct tca atg cca agt ttt ccc aag tca tcc tcc tca<br>Gly Tyr Gly Pro Pro Ser Met Pro Ser Phe Pro Lys Ser Ser Ser Ser<br>               545                      550                  555 | 1744 |
| tct tgc tcg tgt tgc tgc ccc ggc aag aag gaa cct aaa gat cca tca<br>Ser Cys Ser Cys Cys Cys Pro Gly Lys Lys Glu Pro Lys Asp Pro Ser<br>560                      565                      570 | 1792 |
| gag ctt tat agg gat gca aaa cgg gaa gaa ctt gat gct gcc atc ttt<br>Glu Leu Tyr Arg Asp Ala Lys Arg Glu Glu Leu Asp Ala Ala Ile Phe<br>               575                      580                  585 | 1840 |
| aac ctt agg gaa att gac aat tat gat gag tat gaa aga tca atg ttg<br>Asn Leu Arg Glu Ile Asp Asn Tyr Asp Glu Tyr Glu Arg Ser Met Leu<br>590                      595                      600 | 1888 |
| atc tct caa aca agc ttt gag aaa act ttt ggc tta tct tca gtc ttc<br>Ile Ser Gln Thr Ser Phe Glu Lys Thr Phe Gly Leu Ser Ser Val Phe<br>605                      610                      615                  620 | 1936 |
| att gaa tct aca cta atg gag aat gga gga gtg gct gaa tct gcc aac<br>Ile Glu Ser Thr Leu Met Glu Asn Gly Gly Val Ala Glu Ser Ala Asn<br>               625                      630                  635 | 1984 |
| cct tcc aca cta atc aag gaa gca att cat gtc atc ggc tgt ggc tat<br>Pro Ser Thr Leu Ile Lys Glu Ala Ile His Val Ile Gly Cys Gly Tyr<br>          640                      645                  650 | 2032 |
| gag gag aag act gca tgg ggg aaa gag att gga tgg ata tat ggt tca<br>Glu Glu Lys Thr Ala Trp Gly Lys Glu Ile Gly Trp Ile Tyr Gly Ser<br>655                      660                      665 | 2080 |
| gtc act gag gat atc tta acc ggc ttc aaa atg cac tgc cga gga tgg<br>Val Thr Glu Asp Ile Leu Thr Gly Phe Lys Met His Cys Arg Gly Trp<br>          670                      675                  680 | 2128 |
| aga tcg att tac tgc atg ccc tta agg cca gca ttc aaa gga tct gca<br>Arg Ser Ile Tyr Cys Met Pro Leu Arg Pro Ala Phe Lys Gly Ser Ala<br>685                      690                      695                  700 | 2176 |
| ccc atc aat ctg tct gat cgg ttg cac cag gtt ctt cga tgg gct ctt<br>Pro Ile Asn Leu Ser Asp Arg Leu His Gln Val Leu Arg Trp Ala Leu<br>               705                      710                  715 | 2224 |
| gga tct gtt gaa att ttc cta agc agg cat tgc cct cta tgg tat ggc<br>Gly Ser Val Glu Ile Phe Leu Ser Arg His Cys Pro Leu Trp Tyr Gly<br>          720                      725                  730 | 2272 |
| ttt gga ggt ggt cgt ctt aaa tgg ctt caa aga cta gca tat ata aac<br>Phe Gly Gly Gly Arg Leu Lys Trp Leu Gln Arg Leu Ala Tyr Ile Asn<br>               735                      740                  745 | 2320 |
| acc att gtc tat cct ttc aca tcc ctt cca ctc att gcc tat tgt tca<br>Thr Ile Val Tyr Pro Phe Thr Ser Leu Pro Leu Ile Ala Tyr Cys Ser<br>750                      755                      760 | 2368 |
| cta cca gca atc tgt ctt ctc aca gga aaa ttt atc ata cca acg ctc<br>Leu Pro Ala Ile Cys Leu Leu Thr Gly Lys Phe Ile Ile Pro Thr Leu<br>765                      770                      775                  780 | 2416 |
| tca aac ctg gca agt gtt ctc ttt ctt ggc ctt ttc ctt tcc att atc<br>Ser Asn Leu Ala Ser Val Leu Phe Leu Gly Leu Phe Leu Ser Ile Ile<br>               785                      790                  795 | 2464 |
| gtg act gct gtt ctc gag ctc cga tgg agt ggt gtc agc att gag gac<br>Val Thr Ala Val Leu Glu Leu Arg Trp Ser Gly Val Ser Ile Glu Asp<br>          800                      805                  810 | 2512 |
| tta tgg cgt aac gag cag ttt tgg gtc atc ggt ggc gtt tca gcc cat<br>Leu Trp Arg Asn Glu Gln Phe Trp Val Ile Gly Gly Val Ser Ala His<br>815                      820                      825 | 2560 |
| ctc ttt gcc gtc ttc caa ggt ttc ctt aag atg ctt gcg ggc att gac<br>Leu Phe Ala Val Phe Gln Gly Phe Leu Lys Met Leu Ala Gly Ile Asp<br>          830                      835                  840 | 2608 |
| acc aac ttt act gtc act gcc aaa gca gct gat gat gca gat ttt ggt<br>Thr Asn Phe Thr Val Thr Ala Lys Ala Ala Asp Asp Ala Asp Phe Gly<br>845                      850                      855                  860 | 2656 |

|  |  |  |  |  |  |  |  |  |  |  |  |  |  |  |  |  |
|---|---|---|---|---|---|---|---|---|---|---|---|---|---|---|---|---|
| gag | ctc | tac | att | gtg | aaa | tgg | act | aca | ctt | cta | atc | cct | cca | aca | aca | 2704 |
| Glu | Leu | Tyr | Ile | Val | Lys | Trp | Thr | Thr | Leu | Leu | Ile | Pro | Pro | Thr | Thr |  |
|  |  |  |  | 865 |  |  |  | 870 |  |  |  |  | 875 |  |  |  |
| ctc | ctc | atc | gtc | aac | atg | gtt | ggt | gtc | gtt | gcc | gga | ttc | tcc | gat | gcc | 2752 |
| Leu | Leu | Ile | Val | Asn | Met | Val | Gly | Val | Val | Ala | Gly | Phe | Ser | Asp | Ala |  |
|  |  |  | 880 |  |  |  |  | 885 |  |  |  |  | 890 |  |  |  |
| ctc | aac | aaa | ggg | tac | gaa | gct | tgg | gga | cca | ctc | ttt | ggc | aaa | gtg | ttc | 2800 |
| Leu | Asn | Lys | Gly | Tyr | Glu | Ala | Trp | Gly | Pro | Leu | Phe | Gly | Lys | Val | Phe |  |
|  |  | 895 |  |  |  |  | 900 |  |  |  |  | 905 |  |  |  |  |
| ttt | tcc | ttc | tgg | gtc | atc | ctc | cat | ctt | tat | cca | ttc | ctc | aaa | ggt | ctt | 2848 |
| Phe | Ser | Phe | Trp | Val | Ile | Leu | His | Leu | Tyr | Pro | Phe | Leu | Lys | Gly | Leu |  |
|  | 910 |  |  |  |  | 915 |  |  |  |  | 920 |  |  |  |  |  |
| atg | gga | cgc | caa | aac | agg | aca | cca | acc | att | gtt | gtc | ctt | tgg | tca | gtg | 2896 |
| Met | Gly | Arg | Gln | Asn | Arg | Thr | Pro | Thr | Ile | Val | Val | Leu | Trp | Ser | Val |  |
| 925 |  |  |  |  | 930 |  |  |  |  | 935 |  |  |  |  | 940 |  |
| ttg | ttg | gct | tct | gtc | ttc | tct | ctt | gtt | tgg | gtt | cgg | atc | aac | ccg | ttt | 2944 |
| Leu | Leu | Ala | Ser | Val | Phe | Ser | Leu | Val | Trp | Val | Arg | Ile | Asn | Pro | Phe |  |
|  |  |  |  | 945 |  |  |  |  | 950 |  |  |  |  | 955 |  |  |
| gtc | agc | acc | gcc | gat | agc | acc | acc | gtg | tca | cag | agc | tgc | att | tcc | att | 2992 |
| Val | Ser | Thr | Ala | Asp | Ser | Thr | Thr | Val | Ser | Gln | Ser | Cys | Ile | Ser | Ile |  |
|  |  |  | 960 |  |  |  |  | 965 |  |  |  |  | 970 |  |  |  |
| gat | tgt | tga | tgatattatg | tgtttcttag | aattgaaatc | attgcaagta |  |  |  |  |  |  |  |  |  | 3041 |
| Asp | Cys |  |  |  |  |  |  |  |  |  |  |  |  |  |  |  |
|  | 975 |  |  |  |  |  |  |  |  |  |  |  |  |  |  |  | agtggactga aacatgtcta ttgactaagt tttgaacagt ttgtacccat tttattctta    3101 gcagtgtgta attttcctaa acaatgctat gaactataca tatttcattg atatttacat    3161 taaatgaaac tacatcagtc tgcagaaaaa aaaaaaaaaa aaaaaa                    3207

<210> SEQ ID NO 2
<211> LENGTH: 974
<212> TYPE: PRT
<213> ORGANISM: Gossypium hirsutum

<400> SEQUENCE: 2

Met Met Glu Ser Gly Val Pro Val Cys His Thr Cys Gly Glu His Val
 1               5                   10                  15

Gly Leu Asn Val Asn Gly Glu Pro Phe Val Ala Cys His Glu Cys Asn
            20                  25                  30

Phe Pro Ile Cys Lys Ser Cys Phe Glu Tyr Asp Leu Lys Glu Gly Gln
        35                  40                  45

Lys Ala Cys Leu Arg Cys Gly Ile Pro Tyr Asp Glu Asn Leu Leu Asp
    50                  55                  60

Asp Val Glu Lys Ala Thr Gly Asp Gln Ser Thr Met Ala Ala His Leu
65                  70                  75                  80

Ser Lys Ser Gln Asp Val Gly Ile His Ala Arg His Ile Ser Ser Val
                85                  90                  95

Ser Thr Leu Asp Ser Glu Met Thr Glu Asp Asn Gly Asn Pro Ile Trp
            100                 105                 110

Lys Asn Arg Val Glu Ser Trp Lys Glu Lys Asn Lys Lys Lys
        115                 120                 125

Pro Ala Thr Thr Lys Val Glu Arg Glu Ala Glu Ile Pro Pro Glu Gln
    130                 135                 140

Gln Met Glu Asp Lys Pro Ala Pro Asp Ala Ser Gln Pro Leu Ser Thr
145                 150                 155                 160

Ile Ile Pro Ile Pro Lys Ser Arg Leu Ala Pro Tyr Arg Thr Val Ile
                165                 170                 175

-continued

```
Ile Met Arg Leu Ile Ile Leu Gly Leu Phe Phe His Tyr Arg Val Thr
            180                 185                 190
Asn Pro Val Asp Ser Ala Phe Gly Leu Trp Leu Thr Ser Val Ile Cys
        195                 200                 205
Glu Ile Trp Phe Ala Phe Ser Trp Val Leu Asp Gln Phe Pro Lys Trp
    210                 215                 220
Tyr Pro Val Asn Arg Glu Thr Tyr Ile Asp Arg Leu Ser Ala Arg Tyr
225                 230                 235                 240
Glu Arg Glu Gly Glu Pro Asn Glu Leu Ala Ala Val Asp Phe Phe Val
                245                 250                 255
Ser Thr Val Asp Pro Leu Lys Glu Pro Pro Leu Ile Thr Ala Asn Thr
            260                 265                 270
Val Leu Ser Ile Leu Ala Leu Asp Tyr Pro Val Asp Lys Val Ser Cys
        275                 280                 285
Tyr Ile Ser Asp Asp Gly Ala Ala Met Leu Thr Phe Glu Ser Leu Val
    290                 295                 300
Glu Thr Ala Asp Phe Ala Arg Lys Trp Val Pro Phe Cys Lys Lys Phe
305                 310                 315                 320
Ser Ile Glu Pro Arg Ala Pro Glu Phe Tyr Phe Ser Gln Lys Ile Asp
                325                 330                 335
Tyr Leu Lys Asp Lys Val Gln Pro Ser Phe Val Lys Glu Arg Arg Ala
            340                 345                 350
Met Lys Arg Asp Tyr Glu Glu Tyr Lys Ile Arg Ile Asn Ala Leu Val
        355                 360                 365
Ala Lys Ala Gln Lys Thr Pro Glu Glu Gly Trp Thr Met Gln Asp Gly
    370                 375                 380
Thr Pro Trp Pro Gly Asn Asn Pro Arg Asp His Pro Gly Met Ile Gln
385                 390                 395                 400
Val Phe Leu Gly Tyr Ser Gly Ala His Asp Ile Glu Gly Asn Glu Leu
                405                 410                 415
Pro Arg Leu Val Tyr Val Ser Arg Glu Lys Arg Pro Gly Tyr Gln His
            420                 425                 430
His Lys Lys Ala Gly Ala Glu Asn Ala Leu Val Arg Val Ser Ala Val
        435                 440                 445
Leu Thr Asn Ala Pro Phe Ile Leu Asn Leu Asp Cys Asp His Tyr Val
    450                 455                 460
Asn Asn Ser Lys Ala Val Arg Glu Ala Met Cys Phe Leu Met Asp Pro
465                 470                 475                 480
Gln Val Gly Arg Asp Val Cys Tyr Val Gln Phe Pro Gln Arg Phe Asp
                485                 490                 495
Gly Ile Asp Arg Ser Asp Arg Tyr Ala Asn Arg Asn Thr Val Phe Phe
            500                 505                 510
Asp Val Asn Met Lys Gly Leu Asp Gly Ile Gln Gly Pro Val Tyr Val
        515                 520                 525
Gly Thr Gly Cys Val Phe Asn Arg Gln Ala Leu Tyr Gly Tyr Gly Pro
    530                 535                 540
Pro Ser Met Pro Ser Phe Pro Lys Ser Ser Ser Ser Cys Ser Cys
545                 550                 555                 560
Cys Cys Pro Gly Lys Lys Glu Pro Lys Asp Pro Ser Glu Leu Tyr Arg
                565                 570                 575
Asp Ala Lys Arg Glu Glu Leu Asp Ala Ala Ile Phe Asn Leu Arg Glu
            580                 585                 590
```

Ile Asp Asn Tyr Asp Glu Tyr Glu Arg Ser Met Leu Ile Ser Gln Thr
            595                 600                 605

Ser Phe Glu Lys Thr Phe Gly Leu Ser Ser Val Phe Ile Glu Ser Thr
    610                 615                 620

Leu Met Glu Asn Gly Gly Val Ala Glu Ser Ala Asn Pro Ser Thr Leu
625                 630                 635                 640

Ile Lys Glu Ala Ile His Val Ile Gly Cys Gly Tyr Glu Glu Lys Thr
                645                 650                 655

Ala Trp Gly Lys Glu Ile Gly Trp Ile Tyr Gly Ser Val Thr Glu Asp
            660                 665                 670

Ile Leu Thr Gly Phe Lys Met His Cys Arg Gly Trp Arg Ser Ile Tyr
        675                 680                 685

Cys Met Pro Leu Arg Pro Ala Phe Lys Gly Ser Ala Pro Ile Asn Leu
    690                 695                 700

Ser Asp Arg Leu His Gln Val Leu Arg Trp Ala Leu Gly Ser Val Glu
705                 710                 715                 720

Ile Phe Leu Ser Arg His Cys Pro Leu Trp Tyr Gly Phe Gly Gly Gly
                725                 730                 735

Arg Leu Lys Trp Leu Gln Arg Leu Ala Tyr Ile Asn Thr Ile Val Tyr
            740                 745                 750

Pro Phe Thr Ser Leu Pro Leu Ile Ala Tyr Cys Ser Leu Pro Ala Ile
        755                 760                 765

Cys Leu Leu Thr Gly Lys Phe Ile Ile Pro Thr Leu Ser Asn Leu Ala
    770                 775                 780

Ser Val Leu Phe Leu Gly Leu Phe Leu Ser Ile Ile Val Thr Ala Val
785                 790                 795                 800

Leu Glu Leu Arg Trp Ser Gly Val Ser Ile Glu Asp Leu Trp Arg Asn
                805                 810                 815

Glu Gln Phe Trp Val Ile Gly Gly Val Ser Ala His Leu Phe Ala Val
            820                 825                 830

Phe Gln Gly Phe Leu Lys Met Leu Ala Gly Ile Asp Thr Asn Phe Thr
        835                 840                 845

Val Thr Ala Lys Ala Ala Asp Asp Ala Asp Phe Gly Glu Leu Tyr Ile
    850                 855                 860

Val Lys Trp Thr Thr Leu Leu Ile Pro Pro Thr Thr Leu Leu Ile Val
865                 870                 875                 880

Asn Met Val Gly Val Val Ala Gly Phe Ser Asp Ala Leu Asn Lys Gly
                885                 890                 895

Tyr Glu Ala Trp Gly Pro Leu Phe Gly Lys Val Phe Phe Ser Phe Trp
            900                 905                 910

Val Ile Leu His Leu Tyr Pro Phe Leu Lys Gly Leu Met Gly Arg Gln
        915                 920                 925

Asn Arg Thr Pro Thr Ile Val Val Leu Trp Ser Val Leu Leu Ala Ser
    930                 935                 940

Val Phe Ser Leu Val Trp Val Arg Ile Asn Pro Phe Val Ser Thr Ala
945                 950                 955                 960

Asp Ser Thr Thr Val Ser Gln Ser Cys Ile Ser Ile Asp Cys
                965                 970

<210> SEQ ID NO 3
<211> LENGTH: 3311
<212> TYPE: DNA
<213> ORGANISM: Gossypium hirsutum
<220> FEATURE:
<221> NAME/KEY: CDS

<220> LOCATION: (23)..(3142)

<400> SEQUENCE: 3

```
ctttcgttct tttggttttg cc atg gct tca acc acc atg gcc gct ggc ttt        52
                         Met Ala Ser Thr Thr Met Ala Ala Gly Phe
                          1               5                  10 ggt tca ctt gct gtt gac gag aat cgg gga tca tcg aca cat caa tca       100
Gly Ser Leu Ala Val Asp Glu Asn Arg Gly Ser Ser Thr His Gln Ser
             15                  20                  25 tca acg aaa ata tgc agg gtg tgt ggg gat aag atc ggg caa aag gaa       148
Ser Thr Lys Ile Cys Arg Val Cys Gly Asp Lys Ile Gly Gln Lys Glu
         30                  35                  40 aac gga caa ccg ttc gtg gct tgt cat gtc tgt gct ttc ccg gtt tgc       196
Asn Gly Gln Pro Phe Val Ala Cys His Val Cys Ala Phe Pro Val Cys
     45                  50                  55 cgt cct tgt tat gaa tat gaa agg agt gaa gga aac cag tgc tgt cct       244
Arg Pro Cys Tyr Glu Tyr Glu Arg Ser Glu Gly Asn Gln Cys Cys Pro
 60                  65                  70 cag tgc aat act cgc tat aag cgt cac aaa ggt agt cca aga att tca       292
Gln Cys Asn Thr Arg Tyr Lys Arg His Lys Gly Ser Pro Arg Ile Ser
 75                  80                  85                  90 gga gat gaa gaa gat gat tca gat caa gat gat ttt gat gat gaa ttt       340
Gly Asp Glu Glu Asp Asp Ser Asp Gln Asp Asp Phe Asp Asp Glu Phe
                 95                 100                 105 cag att aag aac cgc aag gat gac tcc cat cca caa cat gaa aat gag       388
Gln Ile Lys Asn Arg Lys Asp Asp Ser His Pro Gln His Glu Asn Glu
            110                 115                 120 gaa tat aat aat aat aat cat caa tgg cat ccc aat ggt caa gct ttc       436
Glu Tyr Asn Asn Asn Asn His Gln Trp His Pro Asn Gly Gln Ala Phe
        125                 130                 135 tca gtt gcc gga agc acg gcg ggg aag gat ttg gaa ggg gat aaa gag       484
Ser Val Ala Gly Ser Thr Ala Gly Lys Asp Leu Glu Gly Asp Lys Glu
    140                 145                 150 att tac gga agc gaa gaa tgg aaa gaa aga gtt gag aaa tgg aaa gtc       532
Ile Tyr Gly Ser Glu Glu Trp Lys Glu Arg Val Glu Lys Trp Lys Val
155                 160                 165                 170 agg caa gaa aaa aga ggt ttg gta agc aac gat aat ggc gga aat gat       580
Arg Gln Glu Lys Arg Gly Leu Val Ser Asn Asp Asn Gly Gly Asn Asp
                175                 180                 185 cct cct gaa gaa gat gat tat ctc ttg gct gaa gct cgc cag cct cta       628
Pro Pro Glu Glu Asp Asp Tyr Leu Leu Ala Glu Ala Arg Gln Pro Leu
            190                 195                 200 tgg cga aaa gtg cca att tcg tca agt ctg ata agc cct tac cgg ata       676
Trp Arg Lys Val Pro Ile Ser Ser Ser Leu Ile Ser Pro Tyr Arg Ile
        205                 210                 215 gtc atc gtc ctc cga ttc ttc atc ctc gca ttt ttc ctc cgg ttc cgt       724
Val Ile Val Leu Arg Phe Phe Ile Leu Ala Phe Phe Leu Arg Phe Arg
    220                 225                 230 att cta aca ccc gcc tac gac gct tac ccg tta tgg cta atc tct gtc       772
Ile Leu Thr Pro Ala Tyr Asp Ala Tyr Pro Leu Trp Leu Ile Ser Val
235                 240                 245                 250 atc tgc gaa gtt tgg ttc gcc ttc tcc tgg att ctc gat cag ttc cct       820
Ile Cys Glu Val Trp Phe Ala Phe Ser Trp Ile Leu Asp Gln Phe Pro
                255                 260                 265 aaa tgg ttc cct att act cgc gaa act tac ctc gat cgc ctc tcc ttg       868
Lys Trp Phe Pro Ile Thr Arg Glu Thr Tyr Leu Asp Arg Leu Ser Leu
            270                 275                 280 agg ttc gaa cgt gaa gga gag ccc aat caa ctt ggc ccc gtc gac gtc       916
Arg Phe Glu Arg Glu Gly Glu Pro Asn Gln Leu Gly Pro Val Asp Val
        285                 290                 295
```

-continued

| | | |
|---|---|---|
| ttc gtc agt acc gtt gac ctt ctc aag gaa ccc ccc atc ata acc gcc<br>Phe Val Ser Thr Val Asp Leu Leu Lys Glu Pro Pro Ile Ile Thr Ala<br>300                         305                    310 | 964 |
| aac gcg gtt cta tcg atc ttg gcc gtc gat tac ccg gtc gag aaa gtg<br>Asn Ala Val Leu Ser Ile Leu Ala Val Asp Tyr Pro Val Glu Lys Val<br>315                    320                    325                    330 | 1012 |
| tgt tgt tat gtg tcg gac gat ggt gct tcc atg ctt ctt ttc gat tcg<br>Cys Cys Tyr Val Ser Asp Asp Gly Ala Ser Met Leu Leu Phe Asp Ser<br>                  335                    340                    345 | 1060 |
| ttg tct gaa acg gct gag ttc gcg agg aga tgg gtt ccg ttt tgt aag<br>Leu Ser Glu Thr Ala Glu Phe Ala Arg Arg Trp Val Pro Phe Cys Lys<br>          350                    355                    360 | 1108 |
| aag cat aat gtt gag ccc agg gcg ccg gag ttt tat ttc aat gag aag<br>Lys His Asn Val Glu Pro Arg Ala Pro Glu Phe Tyr Phe Asn Glu Lys<br>               365                    370                    375 | 1156 |
| att gat tat ttg aag gac aag gtc cat cct agc ttt gtt aaa gaa cgg<br>Ile Asp Tyr Leu Lys Asp Lys Val His Pro Ser Phe Val Lys Glu Arg<br>380                         385                    390 | 1204 |
| aga gcc atg aaa agg gaa tat gaa gaa ttt aaa gta agg atc aat gca<br>Arg Ala Met Lys Arg Glu Tyr Glu Glu Phe Lys Val Arg Ile Asn Ala<br>395                       400                    405                    410 | 1252 |
| tta gta gca aaa gct cag aag aaa cca gaa gaa gga tgg gtg atg caa<br>Leu Val Ala Lys Ala Gln Lys Lys Pro Glu Glu Gly Trp Val Met Gln<br>               415                    420                    425 | 1300 |
| gat ggc acc cca tgg ccc gga aat aac act cgt gat cat cct gga atg<br>Asp Gly Thr Pro Trp Pro Gly Asn Asn Thr Arg Asp His Pro Gly Met<br>          430                    435                    440 | 1348 |
| att cag gtc tat cta gga agt gcc ggt gca ctc gat gtg gat ggc aaa<br>Ile Gln Val Tyr Leu Gly Ser Ala Gly Ala Leu Asp Val Asp Gly Lys<br>               445                    450                    455 | 1396 |
| gag ctg cct cga ctt gtc tat gtt tct cgt gag aaa cga cct ggt tat<br>Glu Leu Pro Arg Leu Val Tyr Val Ser Arg Glu Lys Arg Pro Gly Tyr<br>460                       465                    470 | 1444 |
| cag cac cat aag aaa gcc ggt gct gag aat gct ctg gtt cga gtt tct<br>Gln His His Lys Lys Ala Gly Ala Glu Asn Ala Leu Val Arg Val Ser<br>475                       480                    485                    490 | 1492 |
| gca gtg ctt act aat gca ccc ttc ata ttg aat ctg gat tgt gat cat<br>Ala Val Leu Thr Asn Ala Pro Phe Ile Leu Asn Leu Asp Cys Asp His<br>               495                    500                    505 | 1540 |
| tac atc aac aat agc aag gcc atg agg gaa gcg atg tgc ttt tta atg<br>Tyr Ile Asn Asn Ser Lys Ala Met Arg Glu Ala Met Cys Phe Leu Met<br>          510                    515                    520 | 1588 |
| gat cct cag ttt gga aag aag ctt tgt tat gtt caa ttt cca cag aga<br>Asp Pro Gln Phe Gly Lys Lys Leu Cys Tyr Val Gln Phe Pro Gln Arg<br>               525                    530                    535 | 1636 |
| ttt gat ggt att gat cgt cat gat cga tat gct aat cga aat gtt gtc<br>Phe Asp Gly Ile Asp Arg His Asp Arg Tyr Ala Asn Arg Asn Val Val<br>540                       545                    550 | 1684 |
| ttc ttt gat atc aac atg ttg gga tta gat gga ctt caa ggc cct gta<br>Phe Phe Asp Ile Asn Met Leu Gly Leu Asp Gly Leu Gln Gly Pro Val<br>555                       560                    565                    570 | 1732 |
| tat gta ggc aca ggg tgt gtt ttc aac agg cag gca ttg tat ggc tac<br>Tyr Val Gly Thr Gly Cys Val Phe Asn Arg Gln Ala Leu Tyr Gly Tyr<br>               575                    580                    585 | 1780 |
| gat cca cca gtc tct gag aaa cga cca aag atg aca tgt gat tgc tgg<br>Asp Pro Pro Val Ser Glu Lys Arg Pro Lys Met Thr Cys Asp Cys Trp<br>          590                    595                    600 | 1828 |
| cct tct tgg tgt tgc tgt tgt tgc gga ggt tct agg aag aaa tca aag<br>Pro Ser Trp Cys Cys Cys Cys Cys Gly Gly Ser Arg Lys Lys Ser Lys | 1876 |

-continued

|     |     | 605 |     |     |     | 610 |     |     |     | 615 |     |     |     |     |     |      |
|-----|-----|-----|-----|-----|-----|-----|-----|-----|-----|-----|-----|-----|-----|-----|-----|------|
| aag | aaa | ggt | gaa | aag | aag | ggc | tta | ctc | gga | ggt | ctt | tta | tac | gga | aaa | 1924 |
| Lys | Lys | Gly | Glu | Lys | Lys | Gly | Leu | Leu | Gly | Gly | Leu | Leu | Tyr | Gly | Lys |      |
|     |     | 620 |     |     |     | 625 |     |     |     | 630 |     |     |     |     |     |      |

| aag | aag | aag | atg | atg | ggc | aaa | aac | tat | gtg | aaa | aaa | ggg | tct | gca | cca | 1972 |
|-----|-----|-----|-----|-----|-----|-----|-----|-----|-----|-----|-----|-----|-----|-----|-----|------|
| Lys | Lys | Lys | Met | Met | Gly | Lys | Asn | Tyr | Val | Lys | Lys | Gly | Ser | Ala | Pro |      |
| 635 |     |     |     | 640 |     |     |     | 645 |     |     |     | 650 |     |     |     |      |

| gtc | ttt | gat | ctc | gaa | gaa | atc | gaa | gaa | ggg | ctt | gaa | gga | tac | gaa | gaa | 2020 |
|-----|-----|-----|-----|-----|-----|-----|-----|-----|-----|-----|-----|-----|-----|-----|-----|------|
| Val | Phe | Asp | Leu | Glu | Glu | Ile | Glu | Glu | Gly | Leu | Glu | Gly | Tyr | Glu | Glu |      |
|     |     |     |     | 655 |     |     |     | 660 |     |     |     | 665 |     |     |     |      |

| ttg | gag | aaa | tcg | aca | tta | atg | tcg | cag | aag | aat | ttc | gag | aaa | cga | ttc | 2068 |
|-----|-----|-----|-----|-----|-----|-----|-----|-----|-----|-----|-----|-----|-----|-----|-----|------|
| Leu | Glu | Lys | Ser | Thr | Leu | Met | Ser | Gln | Lys | Asn | Phe | Glu | Lys | Arg | Phe |      |
|     |     |     | 670 |     |     |     | 675 |     |     |     | 680 |     |     |     |     |      |

| gga | caa | tca | ccg | gtt | ttc | att | gcc | tca | act | ttg | atg | gaa | aat | ggt | ggc | 2116 |
|-----|-----|-----|-----|-----|-----|-----|-----|-----|-----|-----|-----|-----|-----|-----|-----|------|
| Gly | Gln | Ser | Pro | Val | Phe | Ile | Ala | Ser | Thr | Leu | Met | Glu | Asn | Gly | Gly |      |
|     |     | 685 |     |     |     | 690 |     |     |     | 695 |     |     |     |     |     |      |

| ctt | cct | gaa | gga | act | aat | tcc | aca | tca | ctg | att | aaa | gag | gcc | att | cac | 2164 |
|-----|-----|-----|-----|-----|-----|-----|-----|-----|-----|-----|-----|-----|-----|-----|-----|------|
| Leu | Pro | Glu | Gly | Thr | Asn | Ser | Thr | Ser | Leu | Ile | Lys | Glu | Ala | Ile | His |      |
|     | 700 |     |     |     | 705 |     |     |     | 710 |     |     |     |     |     |     |      |

| gta | att | agc | tgt | ggt | tat | gaa | gaa | aaa | act | gag | tgg | ggc | aaa | gag | atc | 2212 |
|-----|-----|-----|-----|-----|-----|-----|-----|-----|-----|-----|-----|-----|-----|-----|-----|------|
| Val | Ile | Ser | Cys | Gly | Tyr | Glu | Glu | Lys | Thr | Glu | Trp | Gly | Lys | Glu | Ile |      |
| 715 |     |     |     | 720 |     |     |     | 725 |     |     |     |     |     |     | 730 |      |

| gga | tgg | att | tat | ggg | tcg | gtg | acg | gaa | gat | ata | tta | aca | ggt | ttc | aag | 2260 |
|-----|-----|-----|-----|-----|-----|-----|-----|-----|-----|-----|-----|-----|-----|-----|-----|------|
| Gly | Trp | Ile | Tyr | Gly | Ser | Val | Thr | Glu | Asp | Ile | Leu | Thr | Gly | Phe | Lys |      |
|     |     |     |     | 735 |     |     |     | 740 |     |     |     |     | 745 |     |     |      |

| atg | cat | tgt | aga | ggg | tgg | aaa | tcg | gtt | tat | tgt | gta | ccg | aaa | aga | ccg | 2308 |
|-----|-----|-----|-----|-----|-----|-----|-----|-----|-----|-----|-----|-----|-----|-----|-----|------|
| Met | His | Cys | Arg | Gly | Trp | Lys | Ser | Val | Tyr | Cys | Val | Pro | Lys | Arg | Pro |      |
|     |     |     | 750 |     |     |     | 755 |     |     |     | 760 |     |     |     |     |      |

| gca | ttc | aaa | ggg | tcc | gct | cca | atc | aat | ctc | tcg | gat | cgg | ttg | cac | caa | 2356 |
|-----|-----|-----|-----|-----|-----|-----|-----|-----|-----|-----|-----|-----|-----|-----|-----|------|
| Ala | Phe | Lys | Gly | Ser | Ala | Pro | Ile | Asn | Leu | Ser | Asp | Arg | Leu | His | Gln |      |
|     | 765 |     |     |     | 770 |     |     |     | 775 |     |     |     |     |     |     |      |

| gtt | ttg | aga | tgg | gca | ctt | ggt | tct | gta | gaa | att | ttc | ctt | agt | cgt | cac | 2404 |
|-----|-----|-----|-----|-----|-----|-----|-----|-----|-----|-----|-----|-----|-----|-----|-----|------|
| Val | Leu | Arg | Trp | Ala | Leu | Gly | Ser | Val | Glu | Ile | Phe | Leu | Ser | Arg | His |      |
| 780 |     |     |     | 785 |     |     |     | 790 |     |     |     |     |     |     |     |      |

| tgt | cca | ctt | tgg | tat | ggt | tat | ggt | gga | aaa | ctg | aaa | tgg | ctc | gag | agg | 2452 |
|-----|-----|-----|-----|-----|-----|-----|-----|-----|-----|-----|-----|-----|-----|-----|-----|------|
| Cys | Pro | Leu | Trp | Tyr | Gly | Tyr | Gly | Gly | Lys | Leu | Lys | Trp | Leu | Glu | Arg |      |
| 795 |     |     |     | 800 |     |     |     | 805 |     |     |     |     |     |     | 810 |      |

| ctt | gct | tat | atc | aac | acc | att | gtt | tac | cct | ttc | acc | tcg | atc | cct | tta | 2500 |
|-----|-----|-----|-----|-----|-----|-----|-----|-----|-----|-----|-----|-----|-----|-----|-----|------|
| Leu | Ala | Tyr | Ile | Asn | Thr | Ile | Val | Tyr | Pro | Phe | Thr | Ser | Ile | Pro | Leu |      |
|     |     |     | 815 |     |     |     | 820 |     |     |     | 825 |     |     |     |     |      |

| ctc | gcc | tat | tgt | act | att | cca | gct | gtt | tgt | ctt | ctc | acc | ggc | aaa | ttc | 2548 |
|-----|-----|-----|-----|-----|-----|-----|-----|-----|-----|-----|-----|-----|-----|-----|-----|------|
| Leu | Ala | Tyr | Cys | Thr | Ile | Pro | Ala | Val | Cys | Leu | Leu | Thr | Gly | Lys | Phe |      |
|     |     |     | 830 |     |     |     | 835 |     |     |     | 840 |     |     |     |     |      |

| atc | att | cca | act | cta | agc | aac | ctt | aca | agt | gtg | tgg | ttc | ttg | gca | ctt | 2596 |
|-----|-----|-----|-----|-----|-----|-----|-----|-----|-----|-----|-----|-----|-----|-----|-----|------|
| Ile | Ile | Pro | Thr | Leu | Ser | Asn | Leu | Thr | Ser | Val | Trp | Phe | Leu | Ala | Leu |      |
|     |     |     | 845 |     |     |     | 850 |     |     |     | 855 |     |     |     |     |      |

| ttc | ctc | tcc | atc | att | gca | act | gga | gtg | ctt | gaa | ctt | cga | tgg | agc | ggg | 2644 |
|-----|-----|-----|-----|-----|-----|-----|-----|-----|-----|-----|-----|-----|-----|-----|-----|------|
| Phe | Leu | Ser | Ile | Ile | Ala | Thr | Gly | Val | Leu | Glu | Leu | Arg | Trp | Ser | Gly |      |
|     |     | 860 |     |     |     | 865 |     |     |     | 870 |     |     |     |     |     |      |

| gtt | agc | atc | caa | gac | tgg | tgg | cgc | aat | gaa | caa | ttc | tgg | gtg | atc | gga | 2692 |
|-----|-----|-----|-----|-----|-----|-----|-----|-----|-----|-----|-----|-----|-----|-----|-----|------|
| Val | Ser | Ile | Gln | Asp | Trp | Trp | Arg | Asn | Glu | Gln | Phe | Trp | Val | Ile | Gly |      |
| 875 |     |     |     | 880 |     |     |     | 885 |     |     |     |     |     |     | 890 |      |

| ggt | gtc | tcc | gcc | cat | ctt | ttt | gct | gtc | ttc | cag | ggc | ctc | ctc | aaa | gtc | 2740 |
|-----|-----|-----|-----|-----|-----|-----|-----|-----|-----|-----|-----|-----|-----|-----|-----|------|
| Gly | Val | Ser | Ala | His | Leu | Phe | Ala | Val | Phe | Gln | Gly | Leu | Leu | Lys | Val |      |
|     |     |     |     | 895 |     |     |     | 900 |     |     |     | 905 |     |     |     |      |

| cta | gct | gga | gta | gac | acc | aac | ttc | acc | gta | aca | gca | aaa | gca | gca | gac | 2788 |
|-----|-----|-----|-----|-----|-----|-----|-----|-----|-----|-----|-----|-----|-----|-----|-----|------|
| Leu | Ala | Gly | Val | Asp | Thr | Asn | Phe | Thr | Val | Thr | Ala | Lys | Ala | Ala | Asp |      |
|     |     | 910 |     |     |     | 915 |     |     |     | 920 |     |     |     |     |     |      |

| gat | aca | gaa | ttc | ggt | gaa | ctt | tat | ctc | ttc | aaa | tgg | aca | act | ctc | tta | 2836 |

-continued

```
Asp Thr Glu Phe Gly Glu Leu Tyr Leu Phe Lys Trp Thr Thr Leu Leu
    925                 930                 935 atc cct ccc aca act ctg ata ata ctg aac atg gtc gga gtc gtg gcc     2884
Ile Pro Pro Thr Thr Leu Ile Ile Leu Asn Met Val Gly Val Val Ala
    940                 945                 950 gga gtt tca gac gca atc aac aac ggc tat ggt tca tgg ggt cca ttg     2932
Gly Val Ser Asp Ala Ile Asn Asn Gly Tyr Gly Ser Trp Gly Pro Leu
955                 960                 965                 970 ttc ggc aaa ctg ttc ttc gca ttc tgg gtc att ctt cat ctt tac cca     2980
Phe Gly Lys Leu Phe Phe Ala Phe Trp Val Ile Leu His Leu Tyr Pro
                975                 980                 985 ttc ctc aaa ggt ttg atg ggg aga caa aac agg acg ccc acc att gtt     3028
Phe Leu Lys Gly Leu Met Gly Arg Gln Asn Arg Thr Pro Thr Ile Val
        990                 995                 1000 gtg ctt tgg tcc ata ctt ttg gca tcg att ttc tca ctg gtt tgg gta     3076
Val Leu Trp Ser Ile Leu Leu Ala Ser Ile Phe Ser Leu Val Trp Val
    1005                1010                1015 cgg atc gat ccc ttc ttg ccc aaa caa aca ggt cca gtt ctt aaa caa     3124
Arg Ile Asp Pro Phe Leu Pro Lys Gln Thr Gly Pro Val Leu Lys Gln
    1020                1025                1030 tgt ggc gtg gag tgc taa atggtgtttt acaaaccttt cttattattt            3172
Cys Gly Val Glu Cys
1035                1040 tattttccct ttttgccact actgttgatt tgctgtgatt ctaaaaggga tttatcttgt   3232
ttgtaaaaag tctcctatga ttttgttggt tcaatttaat ttctatatgg taaaaaaata   3292
tttctttaaa ttaactata                                                3311

<210> SEQ ID NO 4
<211> LENGTH: 1039
<212> TYPE: PRT
<213> ORGANISM: Gossypium hirsutum

<400> SEQUENCE: 4

Met Ala Ser Thr Thr Met Ala Ala Gly Phe Gly Ser Leu Ala Val Asp
1               5                   10                  15

Glu Asn Arg Gly Ser Ser Thr His Gln Ser Ser Thr Lys Ile Cys Arg
            20                  25                  30

Val Cys Gly Asp Lys Ile Gly Gln Lys Glu Asn Gly Gln Pro Phe Val
        35                  40                  45

Ala Cys His Val Cys Ala Phe Pro Val Cys Arg Pro Cys Tyr Glu Tyr
    50                  55                  60

Glu Arg Ser Glu Gly Asn Gln Cys Cys Pro Gln Cys Asn Thr Arg Tyr
65                  70                  75                  80

Lys Arg His Lys Gly Ser Pro Arg Ile Ser Gly Asp Glu Glu Asp Asp
                85                  90                  95

Ser Asp Gln Asp Asp Phe Asp Asp Glu Phe Gln Ile Lys Asn Arg Lys
            100                 105                 110

Asp Asp Ser His Pro Gln His Glu Asn Glu Glu Tyr Asn Asn Asn Asn
        115                 120                 125

His Gln Trp His Pro Asn Gly Gln Ala Phe Ser Val Ala Gly Ser Thr
    130                 135                 140

Ala Gly Lys Asp Leu Glu Gly Asp Lys Glu Ile Tyr Gly Ser Glu Glu
145                 150                 155                 160

Trp Lys Glu Arg Val Glu Lys Trp Lys Val Arg Gln Glu Lys Arg Gly
                165                 170                 175

Leu Val Ser Asn Asp Asn Gly Gly Asn Asp Pro Pro Glu Glu Asp Asp
```

-continued

```
                180                 185                 190
Tyr Leu Leu Ala Glu Ala Arg Gln Pro Leu Trp Arg Lys Val Pro Ile
        195                 200                 205
Ser Ser Ser Leu Ile Ser Pro Tyr Arg Ile Val Ile Val Leu Arg Phe
210                 215                 220
Phe Ile Leu Ala Phe Phe Leu Arg Phe Arg Ile Leu Thr Pro Ala Tyr
225                 230                 235                 240
Asp Ala Tyr Pro Leu Trp Leu Ile Ser Val Ile Cys Glu Val Trp Phe
                245                 250                 255
Ala Phe Ser Trp Ile Leu Asp Gln Phe Pro Lys Trp Phe Pro Ile Thr
                260                 265                 270
Arg Glu Thr Tyr Leu Asp Arg Leu Ser Leu Arg Phe Glu Arg Glu Gly
                275                 280                 285
Glu Pro Asn Gln Leu Gly Pro Val Asp Val Phe Val Ser Thr Val Asp
290                 295                 300
Leu Leu Lys Glu Pro Pro Ile Ile Thr Ala Asn Ala Val Leu Ser Ile
305                 310                 315                 320
Leu Ala Val Asp Tyr Pro Val Glu Lys Val Cys Cys Tyr Val Ser Asp
                325                 330                 335
Asp Gly Ala Ser Met Leu Leu Phe Asp Ser Leu Ser Glu Thr Ala Glu
                340                 345                 350
Phe Ala Arg Arg Trp Val Pro Phe Cys Lys Lys His Asn Val Glu Pro
                355                 360                 365
Arg Ala Pro Glu Phe Tyr Phe Asn Glu Lys Ile Asp Tyr Leu Lys Asp
                370                 375                 380
Lys Val His Pro Ser Phe Val Lys Glu Arg Arg Ala Met Lys Arg Glu
385                 390                 395                 400
Tyr Glu Glu Phe Lys Val Arg Ile Asn Ala Leu Val Ala Lys Ala Gln
                405                 410                 415
Lys Lys Pro Glu Glu Gly Trp Val Met Gln Asp Gly Thr Pro Trp Pro
                420                 425                 430
Gly Asn Asn Thr Arg Asp His Pro Gly Met Ile Gln Val Tyr Leu Gly
                435                 440                 445
Ser Ala Gly Ala Leu Asp Val Asp Gly Lys Glu Leu Pro Arg Leu Val
450                 455                 460
Tyr Val Ser Arg Glu Lys Arg Pro Gly Tyr Gln His His Lys Lys Ala
465                 470                 475                 480
Gly Ala Glu Asn Ala Leu Val Arg Val Ser Ala Val Leu Thr Asn Ala
                485                 490                 495
Pro Phe Ile Leu Asn Leu Asp Cys Asp His Tyr Ile Asn Asn Ser Lys
                500                 505                 510
Ala Met Arg Glu Ala Met Cys Phe Leu Met Asp Pro Gln Phe Gly Lys
                515                 520                 525
Lys Leu Cys Tyr Val Gln Phe Pro Gln Arg Phe Asp Gly Ile Asp Arg
                530                 535                 540
His Asp Arg Tyr Ala Asn Arg Asn Val Val Phe Phe Asp Ile Asn Met
545                 550                 555                 560
Leu Gly Leu Asp Gly Leu Gln Gly Pro Val Tyr Val Gly Thr Gly Cys
                565                 570                 575
Val Phe Asn Arg Gln Ala Leu Tyr Gly Tyr Asp Pro Val Ser Glu
                580                 585                 590
Lys Arg Pro Lys Met Thr Cys Asp Cys Trp Pro Ser Trp Cys Cys Cys
                595                 600                 605
```

```
Cys Cys Gly Gly Ser Arg Lys Lys Ser Lys Lys Gly Glu Lys Lys
    610                 615                 620
Gly Leu Gly Gly Leu Leu Tyr Gly Lys Lys Lys Met Met Gly
625                 630                 635                 640
Lys Asn Tyr Val Lys Lys Gly Ser Ala Pro Val Phe Asp Leu Glu Glu
                645                 650                 655
Ile Glu Glu Gly Leu Glu Gly Tyr Glu Glu Leu Glu Lys Ser Thr Leu
                660                 665                 670
Met Ser Gln Lys Asn Phe Glu Lys Arg Phe Gly Gln Ser Pro Val Phe
                675                 680                 685
Ile Ala Ser Thr Leu Met Glu Asn Gly Gly Leu Pro Glu Gly Thr Asn
    690                 695                 700
Ser Thr Ser Leu Ile Lys Glu Ala Ile His Val Ile Ser Cys Gly Tyr
705                 710                 715                 720
Glu Glu Lys Thr Glu Trp Gly Lys Glu Ile Gly Trp Ile Tyr Gly Ser
                725                 730                 735
Val Thr Glu Asp Ile Leu Thr Gly Phe Lys Met His Cys Arg Gly Trp
                740                 745                 750
Lys Ser Val Tyr Cys Val Pro Lys Arg Pro Ala Phe Lys Gly Ser Ala
    755                 760                 765
Pro Ile Asn Leu Ser Asp Arg Leu His Gln Val Leu Arg Trp Ala Leu
    770                 775                 780
Gly Ser Val Glu Ile Phe Leu Ser Arg His Cys Pro Leu Trp Tyr Gly
785                 790                 795                 800
Tyr Gly Gly Lys Leu Lys Trp Leu Glu Arg Leu Ala Tyr Ile Asn Thr
                805                 810                 815
Ile Val Tyr Pro Phe Thr Ser Ile Pro Leu Leu Ala Tyr Cys Thr Ile
                820                 825                 830
Pro Ala Val Cys Leu Leu Thr Gly Lys Phe Ile Ile Pro Thr Leu Ser
                835                 840                 845
Asn Leu Thr Ser Val Trp Phe Leu Ala Leu Phe Leu Ser Ile Ile Ala
    850                 855                 860
Thr Gly Val Leu Glu Leu Arg Trp Ser Gly Val Ser Ile Gln Asp Trp
865                 870                 875                 880
Trp Arg Asn Glu Gln Phe Trp Val Ile Gly Gly Val Ser Ala His Leu
                885                 890                 895
Phe Ala Val Phe Gln Gly Leu Leu Lys Val Leu Ala Gly Val Asp Thr
                900                 905                 910
Asn Phe Thr Val Thr Ala Lys Ala Ala Asp Asp Thr Glu Phe Gly Glu
    915                 920                 925
Leu Tyr Leu Phe Lys Trp Thr Thr Leu Leu Ile Pro Pro Thr Thr Leu
    930                 935                 940
Ile Ile Leu Asn Met Val Gly Val Val Ala Gly Val Ser Asp Ala Ile
945                 950                 955                 960
Asn Asn Gly Tyr Gly Ser Trp Gly Pro Leu Phe Gly Lys Leu Phe Phe
                965                 970                 975
Ala Phe Trp Val Ile Leu His Leu Tyr Pro Phe Leu Lys Gly Leu Met
                980                 985                 990
Gly Arg Gln Asn Arg Thr Pro Thr Ile Val Val Leu Trp Ser Ile Leu
                995                 1000                1005
Leu Ala Ser Ile Phe Ser Leu Val Trp Val Arg Ile Asp Pro Phe Leu
    1010                1015                1020
```

```
Pro Lys Gln Thr Gly Pro Val Leu Lys Gln Cys Gly Val Glu Cys
1025                1030                1035
```

<210> SEQ ID NO 5
<211> LENGTH: 2033
<212> TYPE: DNA
<213> ORGANISM: Gossypium hirsutum
<220> FEATURE:
<221> NAME/KEY: CDS
<222> LOCATION: (1)..(1857)

<400> SEQUENCE: 5

```
ccg aca ttc gtg aag gag cgt cga gct atg aag aga gaa tat gaa gaa      48
Pro Thr Phe Val Lys Glu Arg Arg Ala Met Lys Arg Glu Tyr Glu Glu
  1               5                  10                  15 ttc aag gtt agg ata aat gca ctt gta gcc aaa gcc caa aag gtt cct      96
Phe Lys Val Arg Ile Asn Ala Leu Val Ala Lys Ala Gln Lys Val Pro
             20                  25                  30 cca gaa ggg tgg atc atg caa gat ggg aca cca tgg cca gga aac aat     144
Pro Glu Gly Trp Ile Met Gln Asp Gly Thr Pro Trp Pro Gly Asn Asn
         35                  40                  45 act aaa gat cac cct ggt atg att caa gta ttt ctc ggt caa agt gga     192
Thr Lys Asp His Pro Gly Met Ile Gln Val Phe Leu Gly Gln Ser Gly
     50                  55                  60 ggc cat gat acc gaa gga aat gag ctt cct cgt ctc gtc tat gta tct     240
Gly His Asp Thr Glu Gly Asn Glu Leu Pro Arg Leu Val Tyr Val Ser
 65                  70                  75                  80 cga gag aaa agg cct ggt ttc ttg cat cac aag aaa gct ggt gcc atg     288
Arg Glu Lys Arg Pro Gly Phe Leu His His Lys Lys Ala Gly Ala Met
                 85                  90                  95 aac gcc ctt gtt cgg gtc tcg ggg gtg ctc aca aat gct cct ttt atg     336
Asn Ala Leu Val Arg Val Ser Gly Val Leu Thr Asn Ala Pro Phe Met
            100                 105                 110 ttg aac ttg gat tgt gac cat tat tta aat aac agc aag gct gta aga     384
Leu Asn Leu Asp Cys Asp His Tyr Leu Asn Asn Ser Lys Ala Val Arg
        115                 120                 125 gag gct atg tgt ttc ttg atg gac cct caa att gga aga aag gtt tgc     432
Glu Ala Met Cys Phe Leu Met Asp Pro Gln Ile Gly Arg Lys Val Cys
    130                 135                 140 tat gtc caa ttc cct caa cgt ttc gat ggt att gat aga cat gat cga     480
Tyr Val Gln Phe Pro Gln Arg Phe Asp Gly Ile Asp Arg His Asp Arg
145                 150                 155                 160 tat gcc aat cgg aac aca gtt ttc ttt gat att aac atg aaa ggt cta     528
Tyr Ala Asn Arg Asn Thr Val Phe Phe Asp Ile Asn Met Lys Gly Leu
                165                 170                 175 gat ggt ata caa ggc cct gta tat gtc ggc acg ggg tgt gtt ttc aga     576
Asp Gly Ile Gln Gly Pro Val Tyr Val Gly Thr Gly Cys Val Phe Arg
            180                 185                 190 agg caa gct ctt tat ggt tat gaa cct cca aag gga cct aag cgc ccg     624
Arg Gln Ala Leu Tyr Gly Tyr Glu Pro Pro Lys Gly Pro Lys Arg Pro
        195                 200                 205 aaa atg gta acc tgt ggt tgc tgc cct tgt ttt gga cgc cgc aga aag     672
Lys Met Val Thr Cys Gly Cys Cys Pro Cys Phe Gly Arg Arg Arg Lys
    210                 215                 220 gac aaa aag cac tct aag gat ggt gga aat gca aat ggt cta agc cta     720
Asp Lys Lys His Ser Lys Asp Gly Gly Asn Ala Asn Gly Leu Ser Leu
225                 230                 235                 240 gaa gca gcc aaa gat gac aag gag tta ttg atg tcc cac atg aac ttt     768
Glu Ala Ala Lys Asp Asp Lys Glu Leu Leu Met Ser His Met Asn Phe
                245                 250                 255 gaa aag aaa ttt gga caa tca gcc att ttt gta act tca aca ctg atg     816
```

-continued

```
                Glu Lys Lys Phe Gly Gln Ser Ala Ile Phe Val Thr Ser Thr Leu Met
                            260                 265                 270 gaa caa ggt ggt gtc cct cct tct tca agc ccc gca gct ttg ctc aaa          864
Glu Gln Gly Gly Val Pro Pro Ser Ser Ser Pro Ala Ala Leu Leu Lys
275                 280                 285 gaa gcc att cat gta att agt tgt ggt tat gaa gac aaa aca gaa tgg          912
Glu Ala Ile His Val Ile Ser Cys Gly Tyr Glu Asp Lys Thr Glu Trp
    290                 295                 300 gga agc gag ctt ggc tgg att tac ggc tcg att aca gaa gat atc tta          960
Gly Ser Glu Leu Gly Trp Ile Tyr Gly Ser Ile Thr Glu Asp Ile Leu
305                 310                 315                 320 aca gga ttc aag atg cat tgc cgt gga tgg aga tca ata tac tgc atg        1008
Thr Gly Phe Lys Met His Cys Arg Gly Trp Arg Ser Ile Tyr Cys Met
                325                 330                 335 cca aag ttg cct gca ttc aag ggt tca gct ccc atc aat cta tcg gat        1056
Pro Lys Leu Pro Ala Phe Lys Gly Ser Ala Pro Ile Asn Leu Ser Asp
            340                 345                 350 cgt cta aac caa gtc ctt cga tgg gca ctc ggt tct gtt gaa att ttc        1104
Arg Leu Asn Gln Val Leu Arg Trp Ala Leu Gly Ser Val Glu Ile Phe
        355                 360                 365 ttt agt cat cat tgc cca gca tgg tat ggt ttc aag gga gga aag cta        1152
Phe Ser His His Cys Pro Ala Trp Tyr Gly Phe Lys Gly Gly Lys Leu
370                 375                 380 aaa tgg ctt gaa cga ttc gca tat gtc aac aca acc atc tac ccc ttc        1200
Lys Trp Leu Glu Arg Phe Ala Tyr Val Asn Thr Thr Ile Tyr Pro Phe
385                 390                 395                 400 aca tct tta cca ctt ctc gcc tat tgt acc cta ccg gca atc tgt tta        1248
Thr Ser Leu Pro Leu Leu Ala Tyr Cys Thr Leu Pro Ala Ile Cys Leu
                405                 410                 415 ctt acc gat aaa ttt atc atg cca ccg ata agc acc ttt gca agt cta        1296
Leu Thr Asp Lys Phe Ile Met Pro Pro Ile Ser Thr Phe Ala Ser Leu
            420                 425                 430 ttc ttc att gcc ttg ttt ctt tca atc ttt gca act ggt att ctc gag        1344
Phe Phe Ile Ala Leu Phe Leu Ser Ile Phe Ala Thr Gly Ile Leu Glu
        435                 440                 445 cta agg tgg agt gga gta agc att gaa gaa tgg tgg agg aat gag caa        1392
Leu Arg Trp Ser Gly Val Ser Ile Glu Glu Trp Trp Arg Asn Glu Gln
450                 455                 460 ttt tgg gtc atc ggt ggc att tcg gca cat ttg ttc gct gtt atc caa        1440
Phe Trp Val Ile Gly Gly Ile Ser Ala His Leu Phe Ala Val Ile Gln
465                 470                 475                 480 ggc ttg ttg aaa gtt cta gct ggt att gac act aat ttc act gtc aca        1488
Gly Leu Leu Lys Val Leu Ala Gly Ile Asp Thr Asn Phe Thr Val Thr
                485                 490                 495 tcc aag gca act gat gac gag gag ttc ggg gaa ttg tat act ttc aaa        1536
Ser Lys Ala Thr Asp Asp Glu Glu Phe Gly Glu Leu Tyr Thr Phe Lys
            500                 505                 510 tgg aca acc ctt cta att cct cct act acc gtc tta atc atc aat tta        1584
Trp Thr Thr Leu Leu Ile Pro Pro Thr Thr Val Leu Ile Ile Asn Leu
        515                 520                 525 gtc ggt gtc gtt gca ggc atc tcg gat gcc ata aac aat gga tac caa        1632
Val Gly Val Val Ala Gly Ile Ser Asp Ala Ile Asn Asn Gly Tyr Gln
530                 535                 540 tca tgg gga cct ctt ttt ggg aag ctc ttc ttc tct ttc tgg gtg att        1680
Ser Trp Gly Pro Leu Phe Gly Lys Leu Phe Phe Ser Phe Trp Val Ile
545                 550                 555                 560 gtc cat ctc tat cca ttc ctc aaa ggt tta atg ggg aga caa aac cgg        1728
Val His Leu Tyr Pro Phe Leu Lys Gly Leu Met Gly Arg Gln Asn Arg
                565                 570                 575
```

```
aca cca acc att gtt gtt ata tgg tca gtg cta ttg gct tca atc ttc    1776
Thr Pro Thr Ile Val Val Ile Trp Ser Val Leu Leu Ala Ser Ile Phe
        580                 585                 590 tcc ttg ctt tgg gtc cga att gat cca ttt gtg atg aaa acc aaa gga    1824
Ser Leu Leu Trp Val Arg Ile Asp Pro Phe Val Met Lys Thr Lys Gly
            595                 600                 605 cca gac act aca atg tgt ggc att aac tgt tga aaaaaaatca tcttgcgtgg  1877
Pro Asp Thr Thr Met Cys Gly Ile Asn Cys
        610                 615 ttcttttaga ttatggtatg tgatgtatga acaaacaaga atggagatgc acaagacaga  1937
ataaaattag agtgaaagtt ttgtgtagtt atatattcat tctaccaact ataagttttg  1997
tcattcaatt gaaatagct caactttgtg atcaaa                             2033

<210> SEQ ID NO 6
<211> LENGTH: 618
<212> TYPE: PRT
<213> ORGANISM: Gossypium hirsutum

<400> SEQUENCE: 6

Pro Thr Phe Val Lys Glu Arg Arg Ala Met Lys Arg Glu Tyr Glu Glu
  1               5                  10                  15

Phe Lys Val Arg Ile Asn Ala Leu Val Ala Lys Ala Gln Lys Val Pro
             20                  25                  30

Pro Glu Gly Trp Ile Met Gln Asp Gly Thr Pro Trp Pro Gly Asn Asn
         35                  40                  45

Thr Lys Asp His Pro Gly Met Ile Gln Val Phe Leu Gly Gln Ser Gly
     50                  55                  60

Gly His Asp Thr Glu Gly Asn Glu Leu Pro Arg Leu Val Tyr Val Ser
 65                  70                  75                  80

Arg Glu Lys Arg Pro Gly Phe Leu His His Lys Lys Ala Gly Ala Met
                 85                  90                  95

Asn Ala Leu Val Arg Val Ser Gly Val Leu Thr Asn Ala Pro Phe Met
            100                 105                 110

Leu Asn Leu Asp Cys Asp His Tyr Leu Asn Asn Ser Lys Ala Val Arg
        115                 120                 125

Glu Ala Met Cys Phe Leu Met Asp Pro Gln Ile Gly Arg Lys Val Cys
    130                 135                 140

Tyr Val Gln Phe Pro Gln Arg Phe Asp Gly Ile Asp Arg His Asp Arg
145                 150                 155                 160

Tyr Ala Asn Arg Asn Thr Val Phe Phe Asp Ile Asn Met Lys Gly Leu
                165                 170                 175

Asp Gly Ile Gln Gly Pro Val Tyr Val Gly Thr Gly Cys Val Phe Arg
            180                 185                 190

Arg Gln Ala Leu Tyr Gly Tyr Glu Pro Pro Lys Gly Pro Lys Arg Pro
        195                 200                 205

Lys Met Val Thr Cys Gly Cys Cys Pro Cys Phe Gly Arg Arg Arg Lys
    210                 215                 220

Asp Lys Lys His Ser Lys Asp Gly Gly Asn Ala Asn Gly Leu Ser Leu
225                 230                 235                 240

Glu Ala Ala Lys Asp Asp Lys Glu Leu Leu Met Ser His Met Asn Phe
                245                 250                 255

Glu Lys Lys Phe Gly Gln Ser Ala Ile Phe Val Thr Ser Thr Leu Met
            260                 265                 270

Glu Gln Gly Gly Val Pro Pro Ser Ser Pro Ala Ala Leu Leu Lys
        275                 280                 285
```

```
Glu Ala Ile His Val Ile Ser Cys Gly Tyr Asp Lys Thr Glu Trp
290                 295                 300
Gly Ser Glu Leu Gly Trp Ile Tyr Gly Ser Ile Thr Glu Asp Ile Leu
305                 310                 315                 320
Thr Gly Phe Lys Met His Cys Arg Gly Trp Arg Ser Ile Tyr Cys Met
                325                 330                 335
Pro Lys Leu Pro Ala Phe Lys Gly Ser Ala Pro Ile Asn Leu Ser Asp
            340                 345                 350
Arg Leu Asn Gln Val Leu Arg Trp Ala Leu Gly Ser Val Glu Ile Phe
        355                 360                 365
Phe Ser His His Cys Pro Ala Trp Tyr Gly Phe Lys Gly Lys Leu
    370                 375                 380
Lys Trp Leu Glu Arg Phe Ala Tyr Val Asn Thr Thr Ile Tyr Pro Phe
385                 390                 395                 400
Thr Ser Leu Pro Leu Leu Ala Tyr Cys Thr Leu Pro Ala Ile Cys Leu
                405                 410                 415
Leu Thr Asp Lys Phe Ile Met Pro Pro Ile Ser Thr Phe Ala Ser Leu
            420                 425                 430
Phe Phe Ile Ala Leu Phe Leu Ser Ile Phe Ala Thr Gly Ile Leu Glu
        435                 440                 445
Leu Arg Trp Ser Gly Val Ser Ile Glu Glu Trp Trp Arg Asn Glu Gln
    450                 455                 460
Phe Trp Val Ile Gly Gly Ile Ser Ala His Leu Phe Ala Val Ile Gln
465                 470                 475                 480
Gly Leu Leu Lys Val Leu Ala Gly Ile Asp Thr Asn Phe Thr Val Thr
                485                 490                 495
Ser Lys Ala Thr Asp Asp Glu Glu Phe Gly Glu Leu Tyr Thr Phe Lys
            500                 505                 510
Trp Thr Thr Leu Leu Ile Pro Pro Thr Thr Val Leu Ile Ile Asn Leu
        515                 520                 525
Val Gly Val Val Ala Gly Ile Ser Asp Ala Ile Asn Asn Gly Tyr Gln
    530                 535                 540
Ser Trp Gly Pro Leu Phe Gly Lys Leu Phe Phe Ser Phe Trp Val Ile
545                 550                 555                 560
Val His Leu Tyr Pro Phe Leu Lys Gly Leu Met Gly Arg Gln Asn Arg
                565                 570                 575
Thr Pro Thr Ile Val Val Ile Trp Ser Val Leu Leu Ala Ser Ile Phe
            580                 585                 590
Ser Leu Leu Trp Val Arg Ile Asp Pro Phe Val Met Lys Thr Lys Gly
        595                 600                 605
Pro Asp Thr Thr Met Cys Gly Ile Asn Cys
    610                 615

<210> SEQ ID NO 7
<211> LENGTH: 1086
<212> TYPE: DNA
<213> ORGANISM: Gossypium hirsutum
<220> FEATURE:
<221> NAME/KEY: CDS
<222> LOCATION: (24)..(1085)

<400> SEQUENCE: 7
ggcacgagct ttcatatcct cca atg gaa gcc agc gcc gga ctc gtt gcg ggc      53
                         Met Glu Ala Ser Ala Gly Leu Val Ala Gly
                          1               5                  10
```

-continued

| | |
|---|---|
| tct cac aac cgc aat gaa ctt gtt gtc att cat ggc cat gaa gag cct<br>Ser His Asn Arg Asn Glu Leu Val Val Ile His Gly His Glu Glu Pro<br>            15                    20                25 | 101 |
| aaa cct ctg aag aac ttg gat ggt caa gtt tgt gag att tgt ggt gat<br>Lys Pro Leu Lys Asn Leu Asp Gly Gln Val Cys Glu Ile Cys Gly Asp<br>            30                    35                40 | 149 |
| gaa att ggg ttg acg gtc gat gga gat ctt ttc gtg gcc tgc aac gag<br>Glu Ile Gly Leu Thr Val Asp Gly Asp Leu Phe Val Ala Cys Asn Glu<br>            45                    50                55 | 197 |
| tgt ggt ttt cca gtt tgt agg cct tgt tat gag tat gaa agg aga gaa<br>Cys Gly Phe Pro Val Cys Arg Pro Cys Tyr Glu Tyr Glu Arg Arg Glu<br>60                    65                    70 | 245 |
| ggg agt caa caa tgt cct caa tgc aaa act aga tac aag cgt ctc aag<br>Gly Ser Gln Gln Cys Pro Gln Cys Lys Thr Arg Tyr Lys Arg Leu Lys<br>75                    80                    85                90 | 293 |
| ggg agt ccg agg gtg gag gga gat gaa gat gaa gag gat gtg gat gat<br>Gly Ser Pro Arg Val Glu Gly Asp Glu Asp Glu Glu Asp Val Asp Asp<br>                    95                        100                105 | 341 |
| atc gaa cat gaa ttc aac att gat gat gaa caa aac aag tat aga aat<br>Ile Glu His Glu Phe Asn Ile Asp Asp Glu Gln Asn Lys Tyr Arg Asn<br>                    110                     115                 120 | 389 |
| atc gct gaa tcg atg ctt cat gga aag atg agc tac ggg aga ggc cct<br>Ile Ala Glu Ser Met Leu His Gly Lys Met Ser Tyr Gly Arg Gly Pro<br>          125                    130                     135 | 437 |
| gaa gac gat gaa ggt ttg caa atc cca ccc ggt tta gct ggt gtt cga<br>Glu Asp Asp Glu Gly Leu Gln Ile Pro Pro Gly Leu Ala Gly Val Arg<br>140                     145                     150 | 485 |
| tct cgg ccg gtg agc ggg gag ttc cca ata gga agc tct ctt gct tat<br>Ser Arg Pro Val Ser Gly Glu Phe Pro Ile Gly Ser Ser Leu Ala Tyr<br>155                     160                     165                 170 | 533 |
| ggg gaa cac atg tca aat aaa cga gtt cat cca tat cct atg tct gaa<br>Gly Glu His Met Ser Asn Lys Arg Val His Pro Tyr Pro Met Ser Glu<br>                    175                     180                 185 | 581 |
| cct gga agt gca aga tgg gat gaa aag aaa gag gga gga tgg aga gaa<br>Pro Gly Ser Ala Arg Trp Asp Glu Lys Lys Glu Gly Gly Trp Arg Glu<br>          190                    195                     200 | 629 |
| agg atg gat gat tgg aaa atg cag caa ggg aat ttg ggt cct gaa cct<br>Arg Met Asp Asp Trp Lys Met Gln Gln Gly Asn Leu Gly Pro Glu Pro<br>          205                    210                     215 | 677 |
| gat gat gcc tat gat gct gac atg gct atg ctt gat gaa gct agg cag<br>Asp Asp Ala Tyr Asp Ala Asp Met Ala Met Leu Asp Glu Ala Arg Gln<br>220                     225                     230 | 725 |
| cca ttg tca agg aaa gtg cca att gca tcg agc aaa atc aat cct tat<br>Pro Leu Ser Arg Lys Val Pro Ile Ala Ser Ser Lys Ile Asn Pro Tyr<br>235                     240                     245                 250 | 773 |
| cgt atg gtg att gtg gct cgt cta gtt atc ctt gct ttc ttt ctt cgc<br>Arg Met Val Ile Val Ala Arg Leu Val Ile Leu Ala Phe Phe Leu Arg<br>          255                    260                     265 | 821 |
| tat cgg att ttg aac ccg gta cat gat gca att ggg ctt tgg cta act<br>Tyr Arg Ile Leu Asn Pro Val His Asp Ala Ile Gly Leu Trp Leu Thr<br>          270                    275                     280 | 869 |
| tct gtg atc tgt gaa atc tgg ttt gcc ttt tca tgg atc ctt gat cag<br>Ser Val Ile Cys Glu Ile Trp Phe Ala Phe Ser Trp Ile Leu Asp Gln<br>          285                    290                     295 | 917 |
| ttc cct aaa tgg ttc cct att gac cgc gag acg tat ctc gat cgc ctt<br>Phe Pro Lys Trp Phe Pro Ile Asp Arg Glu Thr Tyr Leu Asp Arg Leu<br>300                     305                     310 | 965 |
| tcc ctc agg tat gag agg gaa ggt gag ccc aac atg ctt gct tct gtt<br>Ser Leu Arg Tyr Glu Arg Glu Gly Glu Pro Asn Met Leu Ala Ser Val<br>315                     320                     325                 330 | 1013 |

```
gat att ttt gtc agt aca gtg gat cca ttg aag gga cct cct cta gta    1061
Asp Ile Phe Val Ser Thr Val Asp Pro Leu Lys Gly Pro Pro Leu Val
            335                 340                 345 aca gcg aat aca gtt cta tcg atc t                                  1086
Thr Ala Asn Thr Val Leu Ser Ile
            350
```

<210> SEQ ID NO 8
<211> LENGTH: 354
<212> TYPE: PRT
<213> ORGANISM: Gossypium hirsutum

<400> SEQUENCE: 8

```
Met Glu Ala Ser Ala Gly Leu Val Ala Gly Ser His Asn Arg Asn Glu
  1               5                  10                  15

Leu Val Val Ile His Gly His Glu Pro Lys Pro Leu Lys Asn Leu
             20                  25                  30

Asp Gly Gln Val Cys Glu Ile Cys Gly Asp Glu Ile Gly Leu Thr Val
         35                  40                  45

Asp Gly Asp Leu Phe Val Ala Cys Asn Glu Cys Gly Phe Pro Val Cys
     50                  55                  60

Arg Pro Cys Tyr Glu Tyr Glu Arg Arg Glu Gly Ser Gln Gln Cys Pro
 65                  70                  75                  80

Gln Cys Lys Thr Arg Tyr Lys Arg Leu Lys Gly Ser Pro Arg Val Glu
                 85                  90                  95

Gly Asp Glu Asp Glu Glu Asp Val Asp Asp Ile Glu His Glu Phe Asn
            100                 105                 110

Ile Asp Asp Glu Gln Asn Lys Tyr Arg Asn Ile Ala Glu Ser Met Leu
        115                 120                 125

His Gly Lys Met Ser Tyr Gly Arg Gly Pro Glu Asp Asp Glu Gly Leu
    130                 135                 140

Gln Ile Pro Pro Gly Leu Ala Gly Val Arg Ser Arg Pro Val Ser Gly
145                 150                 155                 160

Glu Phe Pro Ile Gly Ser Ser Leu Ala Tyr Gly Glu His Met Ser Asn
                165                 170                 175

Lys Arg Val His Pro Tyr Pro Met Ser Glu Pro Gly Ser Ala Arg Trp
            180                 185                 190

Asp Glu Lys Lys Glu Gly Gly Trp Arg Glu Arg Met Asp Asp Trp Lys
        195                 200                 205

Met Gln Gln Gly Asn Leu Gly Pro Glu Pro Asp Asp Ala Tyr Asp Ala
    210                 215                 220

Asp Met Ala Met Leu Asp Glu Ala Arg Gln Pro Leu Ser Arg Lys Val
225                 230                 235                 240

Pro Ile Ala Ser Ser Lys Ile Asn Pro Tyr Arg Met Val Ile Val Ala
                245                 250                 255

Arg Leu Val Ile Leu Ala Phe Phe Leu Arg Tyr Arg Ile Leu Asn Pro
            260                 265                 270

Val His Asp Ala Ile Gly Leu Trp Leu Thr Ser Val Ile Cys Glu Ile
        275                 280                 285

Trp Phe Ala Phe Ser Trp Ile Leu Asp Gln Phe Pro Lys Trp Phe Pro
    290                 295                 300

Ile Asp Arg Glu Thr Tyr Leu Asp Arg Leu Ser Leu Arg Tyr Glu Arg
305                 310                 315                 320

Glu Gly Glu Pro Asn Met Leu Ala Ser Val Asp Ile Phe Val Ser Thr
                325                 330                 335
```

```
Val Asp Pro Leu Lys Gly Pro Pro Leu Val Thr Ala Asn Thr Val Leu
            340                 345                 350

Ser Ile

<210> SEQ ID NO 9
<211> LENGTH: 1000
<212> TYPE: DNA
<213> ORGANISM: Gossypium hirsutum
<220> FEATURE:
<221> NAME/KEY: CDS
<222> LOCATION: (1)..(999)

<400> SEQUENCE: 9 gac aaa gtc cgg ccg aca ttc gtg aag gag cgt cga gct atg aag aga      48
Asp Lys Val Arg Pro Thr Phe Val Lys Glu Arg Arg Ala Met Lys Arg
  1               5                  10                  15 gaa tat gaa gaa ttc aag gtt agg ata aat gca ctt gta gcc aaa gcc      96
Glu Tyr Glu Glu Phe Lys Val Arg Ile Asn Ala Leu Val Ala Lys Ala
             20                  25                  30 caa aag gtt cct cca gaa ggg tgg atc atg caa gat ggg aca cca tgg     144
Gln Lys Val Pro Pro Glu Gly Trp Ile Met Gln Asp Gly Thr Pro Trp
         35                  40                  45 cca gga aac aat act aaa gat cac cct ggt atg att caa gta ttt ctc     192
Pro Gly Asn Asn Thr Lys Asp His Pro Gly Met Ile Gln Val Phe Leu
 50                  55                  60 ggt caa agt gga ggc cat gat acc gaa gga aat gag ctt cct cgt ctc     240
Gly Gln Ser Gly Gly His Asp Thr Glu Gly Asn Glu Leu Pro Arg Leu
 65                  70                  75                  80 gtc tat gta tct cga gag aaa agg cca ggt ttc ttg cat cac aag aaa     288
Val Tyr Val Ser Arg Glu Lys Arg Pro Gly Phe Leu His His Lys Lys
                 85                  90                  95 gct ggt gcc atg aac gcc ctt gtt cgt gtc tcg ggg gtg ctt aca aat     336
Ala Gly Ala Met Asn Ala Leu Val Arg Val Ser Gly Val Leu Thr Asn
            100                 105                 110 gct cct ttt atg ttg aac ttg gat tgt gac cac tat tta aat aac agc     384
Ala Pro Phe Met Leu Asn Leu Asp Cys Asp His Tyr Leu Asn Asn Ser
        115                 120                 125 aag gct gta aga gag gct atg tgt ttc ttg atg gac cct caa att gga     432
Lys Ala Val Arg Glu Ala Met Cys Phe Leu Met Asp Pro Gln Ile Gly
    130                 135                 140 aga aag gtt tgc tat gtc caa ttc cct caa cgt ttc gat ggt att gat     480
Arg Lys Val Cys Tyr Val Gln Phe Pro Gln Arg Phe Asp Gly Ile Asp
145                 150                 155                 160 aga cat gat cga tat gcc aat cgg aac aca gtt ttc ttt gat att aac     528
Arg His Asp Arg Tyr Ala Asn Arg Asn Thr Val Phe Phe Asp Ile Asn
                165                 170                 175 atg aaa ggt cta gat ggt ata caa ggc cct gta tat gtc ggc acg ggg     576
Met Lys Gly Leu Asp Gly Ile Gln Gly Pro Val Tyr Val Gly Thr Gly
            180                 185                 190 tgt gtt ttc aga agg caa gct ctt tat ggt tat gaa cct cca aag gga     624
Cys Val Phe Arg Arg Gln Ala Leu Tyr Gly Tyr Glu Pro Pro Lys Gly
        195                 200                 205 cct aag cgc ccg aaa atg gta acc tgt ggt tgc tgc cct tgc ttt gga     672
Pro Lys Arg Pro Lys Met Val Thr Cys Gly Cys Cys Pro Cys Phe Gly
    210                 215                 220 cgc cgc aga aag gac aaa aag cac tct aag gat ggt gga aat gca aat     720
Arg Arg Arg Lys Asp Lys Lys His Ser Lys Asp Gly Gly Asn Ala Asn
225                 230                 235                 240 ggt cta agc cta gaa gca gcc gaa gat gac aag gag tta ttg atg tcc     768
Gly Leu Ser Leu Glu Ala Ala Glu Asp Asp Lys Glu Leu Leu Met Ser
```

| | | | |
|---|---|---|---|
| | 245 | 250 | 255 | cac atg aac ttt gaa aag aaa ttt gga caa tca gcc att ttt gta act            816
His Met Asn Phe Glu Lys Lys Phe Gly Gln Ser Ala Ile Phe Val Thr
                260                 265                 270 tca aca ctg atg gaa caa ggt ggt gtc cct cct tct tca agc cct gca            864
Ser Thr Leu Met Glu Gln Gly Gly Val Pro Pro Ser Ser Ser Pro Ala
        275                 280                 285 gct ttg ctc aaa gaa gcc att cat gta att agt tgt ggt tat gaa gac            912
Ala Leu Leu Lys Glu Ala Ile His Val Ile Ser Cys Gly Tyr Glu Asp
290                 295                 300 aaa acc gaa tgg gga agc gag ctt ggc tgg att tac ggc tcg att aca            960
Lys Thr Glu Trp Gly Ser Glu Leu Gly Trp Ile Tyr Gly Ser Ile Thr
305                 310                 315                 320 gaa gat atc tta aca ggt ttc aag atg cat tgc cgt gga t                     1000
Glu Asp Ile Leu Thr Gly Phe Lys Met His Cys Arg Gly
                325                 330

<210> SEQ ID NO 10
<211> LENGTH: 333
<212> TYPE: PRT
<213> ORGANISM: Gossypium hirsutum

<400> SEQUENCE: 10

Asp Lys Val Arg Pro Thr Phe Val Lys Glu Arg Arg Ala Met Lys Arg
1               5                   10                  15

Glu Tyr Glu Glu Phe Lys Val Arg Ile Asn Ala Leu Val Ala Lys Ala
                20                  25                  30

Gln Lys Val Pro Pro Glu Gly Trp Ile Met Gln Asp Gly Thr Pro Trp
        35                  40                  45

Pro Gly Asn Asn Thr Lys Asp His Pro Gly Met Ile Gln Val Phe Leu
    50                  55                  60

Gly Gln Ser Gly His Asp Thr Glu Gly Asn Glu Leu Pro Arg Leu
65                  70                  75                  80

Val Tyr Val Ser Arg Glu Lys Arg Pro Gly Phe Leu His His Lys Lys
                85                  90                  95

Ala Gly Ala Met Asn Ala Leu Val Arg Val Ser Gly Val Leu Thr Asn
                100                 105                 110

Ala Pro Phe Met Leu Asn Leu Asp Cys Asp His Tyr Leu Asn Asn Ser
        115                 120                 125

Lys Ala Val Arg Glu Ala Met Cys Phe Leu Met Asp Pro Gln Ile Gly
    130                 135                 140

Arg Lys Val Cys Tyr Val Gln Phe Pro Gln Arg Phe Asp Gly Ile Asp
145                 150                 155                 160

Arg His Asp Arg Tyr Ala Asn Arg Asn Thr Val Phe Phe Asp Ile Asn
                165                 170                 175

Met Lys Gly Leu Asp Gly Ile Gln Gly Pro Val Tyr Val Gly Thr Gly
            180                 185                 190

Cys Val Phe Arg Arg Gln Ala Leu Tyr Gly Tyr Glu Pro Pro Lys Gly
        195                 200                 205

Pro Lys Arg Pro Lys Met Val Thr Cys Gly Cys Pro Cys Phe Gly
    210                 215                 220

Arg Arg Arg Lys Asp Lys Lys His Ser Lys Asp Gly Gly Asn Ala Asn
225                 230                 235                 240

Gly Leu Ser Leu Glu Ala Ala Glu Asp Asp Lys Glu Leu Leu Met Ser
                245                 250                 255

His Met Asn Phe Glu Lys Lys Phe Gly Gln Ser Ala Ile Phe Val Thr

```
            260                 265                 270
Ser Thr Leu Met Glu Gln Gly Gly Val Pro Pro Ser Ser Ser Pro Ala
        275                 280                 285

Ala Leu Leu Lys Glu Ala Ile His Val Ile Ser Cys Gly Tyr Glu Asp
    290                 295                 300

Lys Thr Glu Trp Gly Ser Glu Leu Gly Trp Ile Tyr Gly Ser Ile Thr
305                 310                 315                 320

Glu Asp Ile Leu Thr Gly Phe Lys Met His Cys Arg Gly
                325                 330

<210> SEQ ID NO 11
<211> LENGTH: 622
<212> TYPE: PRT
<213> ORGANISM: Gossypium hirsutum

<400> SEQUENCE: 11

Asp Lys Val Arg Pro Thr Phe Val Lys Glu Arg Ala Met Lys Arg
  1               5                  10                  15

Glu Tyr Glu Glu Phe Lys Val Arg Ile Asn Ala Leu Val Ala Lys Ala
                 20                  25                  30

Gln Lys Val Pro Pro Glu Gly Trp Ile Met Gln Asp Gly Thr Pro Trp
             35                  40                  45

Pro Gly Asn Asn Thr Lys Asp His Pro Gly Met Ile Gln Val Phe Leu
         50                  55                  60

Gly Gln Ser Gly Gly His Asp Thr Glu Gly Asn Glu Leu Pro Arg Leu
 65                  70                  75                  80

Val Tyr Val Ser Arg Glu Lys Arg Pro Gly Phe Leu His His Lys Lys
                 85                  90                  95

Ala Gly Ala Met Asn Ala Leu Val Arg Val Ser Gly Val Leu Thr Asn
            100                 105                 110

Ala Pro Phe Met Leu Asn Leu Asp Cys Asp His Tyr Leu Asn Asn Ser
        115                 120                 125

Lys Ala Val Arg Glu Ala Met Cys Phe Leu Met Asp Pro Gln Ile Gly
    130                 135                 140

Arg Lys Val Cys Tyr Val Gln Phe Pro Gln Arg Phe Asp Gly Ile Asp
145                 150                 155                 160

Arg His Asp Arg Tyr Ala Asn Arg Asn Thr Val Phe Phe Asp Ile Asn
                165                 170                 175

Met Lys Gly Leu Asp Gly Ile Gln Gly Pro Val Tyr Val Gly Thr Gly
            180                 185                 190

Cys Val Phe Arg Arg Gln Ala Leu Tyr Gly Tyr Glu Pro Pro Lys Gly
        195                 200                 205

Pro Lys Arg Pro Lys Met Val Thr Cys Gly Cys Cys Pro Cys Phe Gly
    210                 215                 220

Arg Arg Arg Lys Asp Lys Lys His Ser Lys Asp Gly Gly Asn Ala Asn
225                 230                 235                 240

Gly Leu Ser Leu Glu Ala Ala Xaa Asp Asp Lys Glu Leu Leu Met Ser
                245                 250                 255

His Met Asn Phe Glu Lys Lys Phe Gly Gln Ser Ala Ile Phe Val Thr
            260                 265                 270

Ser Thr Leu Met Glu Gln Gly Gly Val Pro Pro Ser Ser Ser Pro Ala
        275                 280                 285

Ala Leu Leu Lys Glu Ala Ile His Val Ile Ser Cys Gly Tyr Glu Asp
    290                 295                 300
```

```
Lys Thr Glu Trp Gly Ser Glu Leu Gly Trp Ile Tyr Gly Ser Ile Thr
305                 310                 315                 320

Glu Asp Ile Leu Thr Gly Phe Lys Met His Cys Arg Gly Trp Arg Ser
                325                 330                 335

Ile Tyr Cys Met Pro Lys Leu Pro Ala Phe Lys Gly Ser Ala Pro Ile
            340                 345                 350

Asn Leu Ser Asp Arg Leu Asn Gln Val Leu Arg Trp Ala Leu Gly Ser
        355                 360                 365

Val Glu Ile Phe Phe Ser His His Cys Pro Ala Trp Tyr Gly Phe Lys
370                 375                 380

Gly Gly Lys Leu Lys Trp Leu Glu Arg Phe Ala Tyr Val Asn Thr Thr
385                 390                 395                 400

Ile Tyr Pro Phe Thr Ser Leu Pro Leu Leu Ala Tyr Cys Thr Leu Pro
                405                 410                 415

Ala Ile Cys Leu Leu Thr Asp Lys Phe Ile Met Pro Pro Ile Ser Thr
            420                 425                 430

Phe Ala Ser Leu Phe Phe Ile Ala Leu Phe Leu Ser Ile Phe Ala Thr
        435                 440                 445

Gly Ile Leu Glu Leu Arg Trp Ser Gly Val Ser Ile Glu Glu Trp Trp
450                 455                 460

Arg Asn Glu Gln Phe Trp Val Ile Gly Ile Ser Ala His Leu Phe
465                 470                 475                 480

Ala Val Ile Gln Gly Leu Leu Lys Val Leu Ala Gly Ile Asp Thr Asn
                485                 490                 495

Phe Thr Val Thr Ser Lys Ala Thr Asp Asp Glu Glu Phe Gly Glu Leu
            500                 505                 510

Tyr Thr Phe Lys Trp Thr Thr Leu Leu Ile Pro Pro Thr Thr Val Leu
        515                 520                 525

Ile Ile Asn Leu Val Gly Val Val Ala Gly Ile Ser Asp Ala Ile Asn
530                 535                 540

Asn Gly Tyr Gln Ser Trp Gly Pro Leu Phe Gly Lys Leu Phe Phe Ser
545                 550                 555                 560

Phe Trp Val Ile Val His Leu Tyr Pro Phe Leu Lys Gly Leu Met Gly
                565                 570                 575

Arg Gln Asn Arg Thr Pro Thr Ile Val Val Ile Trp Ser Val Leu Leu
            580                 585                 590

Ala Ser Ile Phe Ser Leu Leu Trp Val Arg Ile Asp Pro Phe Val Met
        595                 600                 605

Lys Thr Lys Gly Pro Asp Thr Thr Met Cys Gly Ile Asn Cys
610                 615                 620

<210> SEQ ID NO 12
<211> LENGTH: 9
<212> TYPE: PRT
<213> ORGANISM: Gossypium hirsutum

<400> SEQUENCE: 12

Gln Xaa Xaa Xaa Xaa Xaa Xaa Arg Trp
 1               5

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence:  synthetic
```

```
<400> SEQUENCE: 13
gagagagaga gagagagaga actagtctcg agttttttt tttttttttt                50

<210> SEQ ID NO 14
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 14
aattcggcac gag                                                       13

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 15
gactgaagat aagccaaaag                                                20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: synthetic

<400> SEQUENCE: 16
ggaatgatga atttgccgg                                                 19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 17
tgcaggcaac tttggcatgc                                                20

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: synthetic

<400> SEQUENCE: 18
agcaacacga gcaagatgag gaggatgact                                     30

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: synthetic

<400> SEQUENCE: 19
ccggatcctt caaccttct tcgatttc                                        28

<210> SEQ ID NO 20
<211> LENGTH: 29
```

```
<212> TYPE: DNA
<213> ORGANISM: Artificial Sequence
<220> FEATURE:
<223> OTHER INFORMATION: Description of Artificial Sequence: synthetic

<400> SEQUENCE: 20
ccggatccac ggcaatgcat cttgaaacc                                  29

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: synthetic

<400> SEQUENCE: 21
ggttagcata ttgtttgtag cattggg                                    27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: synthetic

<400> SEQUENCE: 22
atcaatgaaa tatgtatagt tcatagc                                    27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: synthetic

<400> SEQUENCE: 23
ctttcgttct tttggttttg ccatggc                                    27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: synthetic

<400> SEQUENCE: 24 agactttta caaacaagat aaatccc                                     27
```

CELLULOSE SYNTHASE GENE

TECHNICAL FIELD

The present invention relates to a DNA coding for cellulose synthase originating from cotton plant (*Gossypium hirsutum*), a recombinant DNA containing the same, a transformed cell transformed with the DNA, and a method for controlling cellular cellulose synthesis.

BACKGROUND ART

Cellulose is used for paper, woody structural materials, fiber, cloths, food, cosmetics, and pharmaceuticals, as well as it is utilized as energy. Therefore, cellulose is industrially useful and valuable. Cellulose is capable of forming a variety of crystalline structures, and hence it is expected to develop a new material by controlling enzymes involved in biosynthesis of cellulose. The cellulose-related industry has been hitherto directed to such cellulose products that have been already produced, in which there has been no trial to develop a new material based on an aspect of biosynthesis. The mechanism of disease action, which is exerted by pathogenic microorganisms on plants, often results from the inhibition on cellulose biosynthesis as in *Pyricularia oryzae* (*P. oryzae*). Therefore, the addition of disease resistance to the cellulose biosynthesis mechanism is agriculturally applicable and valuable. Further, cellulose is the most abundant organic compound on the earth, and it is a sink in which the largest amount of $CO_2$ in the atmospheric air is fixed. Therefore, the genetic improvement of cellulose biosynthesis enzymes is also applicable to the industry which is directed to the control of $CO_2$ in the atmospheric air based on the use of cellulose as the sink.

In recent years, cDNA's originating from fiber cells of cotton plant have been randomly sequenced, and it has been reported that full length CelA1 and partial length of CelA2 probably represent cDNAs of cotton plant cellulose synthase, in view of the homology to bacterial cellulose synthase gene (bacterial BcsA) (Pear et al., *Proceeding of National Academy of Science, USA* (1996) 93 12637–12642). The binding ability to UDP-glucose has been demonstrated for CelA1. However, as for CelA2, the homology has been merely demonstrated for the C-terminal amino acid sequence.

DISCLOSURE OF THE INVENTION

The present invention has been made in order to provide a new method for regulating cellulose production in prokaryotic cells or eukaryotic cells, an object of which is to provide a DNA coding for cellulose synthase, a recombinant DNA containing the same, a transformed cell transformed with the DNA, and a method for regulating cellular cellulose synthesis.

The present inventors firstly extracted mRNAs at the stage for cotton plant fiber cells to accumulate cellulose, and cDNAs complementary thereto were synthesized to construct a cDNA library. 750 of cDNA clones were arbitrarily selected from the library, and they were randomly subjected to sequencing. Six amino acid sequences were derived for one nucleotide sequence of each of the obtained clones to select those having homology to an amino acid sequence obtained by translation from a gene of cellulose 4-β-glucosyltransferase (bcsA) of cellulose synthase operon of acetobacterium. As a result, genes, which were classified into three types or groups, were found, and they were designated as PcsA1, PcsA2, and PcsA3 respectively (PcsA is an abbreviation of "Plant Cellulose Synthase A").

That is, the present invention lies in a DNA coding for any one of the following proteins (A) to (C):

(A) a protein having a cellulose synthase activity and comprising an amino acid sequence shown in SEQ ID NO: 2 or an amino acid sequence involving deletion, substitution, insertion, or addition of one or several amino acids relevant to SEQ ID NO: 2;

(B) a protein having a cellulose synthase activity and comprising an amino acid sequence shown in SEQ ID NO: 4 or an amino acid sequence involving deletion, substitution, insertion, or addition of one or several amino acids relevant to SEQ ID NO: 4; and (C) a protein having a cellulose synthase activity and comprising an amino acid sequence shown in SEQ ID NO: 8 or an amino acid sequence involving deletion, substitution, insertion, or addition of one or several amino acids relevant to SEQ ID NO: 8, and comprising an amino acid sequence shown in SEQ ID NO: 11 or an amino acid sequence involving deletion, substitution, insertion, or addition of one or several amino acids relevant to SEQ ID NO: 11.

In another aspect, the present invention provides a recombinant vector comprising all or a part of the DNA as defined above, and a transformed cell transformed with the DNA as defined above.

In still another aspect, the present invention provides a method for regulating cellulose synthesis in a cell, comprising the steps of introducing the DNA as defined above into the cell, and expressing RNA having a nucleotide sequence homologous to the DNA as defined above or a nucleotide sequence complementary to the DNA as defined above.

SEQ ID NO: 1 corresponds to a sequence of PcsA1, and SEQ ID NO: 3 corresponds to a sequence of PcsA2. SEQ ID NO: 5 corresponds to a sequence of 3'-side region of PcsA3, SEQ ID NO: 7 corresponds to a sequence of 5'-side region of PcsA3, and SEQ ID NO: 9 corresponds to a sequence of internal region of PcsA3.

It has been demonstrated that PcsA1 and PcsA2 of the DNA's described above are DNA's coding for cotton plant cellulose synthase, according to the expression in eukaryotic cells (animal cells and/or yeast). It has been also demonstrated that an antibody thereagainst inhibits the cotton plant cellulose synthase activity in a cell-free system. Further, PcsA3, which is different from PcsA1 and PcsA2, has been found. Any one of these species was obtained as partial one, at the stage of clones obtained by the random sequencing, and no 5'-portion of the coding region was contained. Therefore, clones which have sequences of 5'-portions were isolated in accordance with the 5'-RACE method based on the use of PCR to determine the sequences. As a result of this operation, the sequences of the 5'-portions corresponding to the partial length clones were obtained for PcsA1 and PcsA2.

On the other hand, as for PcsA3, a sequence of a 5'-portion of another clone, which was considered to belong to the same PcsA3 group, was obtained. The both sequences had extremely high homology, and hence they were considered to have underwent multiple gene formation relatively recently originating from an identical gene through the process of duplication. Therefore, even when the both are combined with each other at corresponding portions to construct a fused gene followed by expression, it is assumed that the activity and function of a produced enzyme may not be affected thereby.

As for PcsA1 and PcsA2, in order to obtain a full length clone, primers were designed on the basis of the sequence of the 5'-portion and the sequence of the 3'-portion of the partial length clone to perform PCR. Thus, a clone containing ORF was obtained.

Those applicable as the template to be used for the RACE method may be any of cDNA synthesized from mRNA and a phage library. When the phage library is used, it is possible to use a sequence in the vector as a 5'-side primer.

As a result of random sequencing, seven clones concerning PcsA2 were most abundantly present, of 15 clones seemed to code the cellulose synthase. Expression was confirmed in eukaryotic cells (animal cells and/or yeast) transformed with the cellulose synthase gene. As a result, the cellulose synthase activity was observed.

The present invention will be explained in detail below.

<1> Preparation of Cotton Plant cDNA Library

Cotton plant fiber cells at the stage of cellulose accumulation are preferably used as a material for extracting mRNA to construct a cotton plant cDNA library. The method for extracting mRNA is not specifically limited, for which it is possible to adopt an ordinary method for extracting mRNA from plant. cDNA can be synthesized, for example, by using a poly T sequence which is complementary to poly A nucleotide existing at the terminal of mRNA as a primer to synthesize complementary DNA by the aid of reverse transcriptase, and forming a double strand by the aid of DNA polymerase.

The method therefor is described, for example, in *Molecular Cloninq* (Maniatis et al., Cold Spring Harbour Laboratory). However, a variety of cDNA synthesis kits are commercially available from various companies, which may be used.

Generally, the library is constructed by using a phage vector. A variety of commercially available vectors are usable. However, it is preferable to use a vector, for example, λZAP vector in which it is unnecessary to perform recloning from the vector, and it is possible to immediately prepare a plasmid for sequencing.

<2> Determination of Nucleotide Sequence of cDNA

Clones are randomly selected from the obtained cDNA library to determine nucleotide sequences of inserts in the clones. The nucleotide sequence can be determined in accordance with the Maxam-Gilbert method or the dideoxy method. Among them, the dideoxy method is more convenient and preferred.

The nucleotide sequence can be determined in accordance with the dideoxy method by using a commercially available sequencing kit. Further, the use of an automatic sequencer makes it possible to determine sequences of a large number of clones for a short period of time.

It is unnecessary to determine the sequence for an entire length of the insert. It is enough to determine a length of nucleotide sequence which is considered to be sufficient to perform homology search. For example, in Examples described later on, the homology search as described below was performed when a sequence having not less than 60 nucleotides was successfully determined.

<3> Homology Search with Gene Data Base

The determined nucleotide sequence of each of cDNA clones is used to perform the homology search with respect to known amino acid sequences of the cellulose synthase or nucleotide sequences of genes coding therefor registered in the gene data base. The cellulose synthase is exemplified by an enzyme encoded by a gene of cellulose 4-β-glucosyltransferase (BcsA) of cellulose synthase operon of acetobacterium (Wong, H. C. et al., *Proc. Natl. Acad. Sci. U.S.A.*, 87, 8130–8134 (1990), ACCESSION No. M37202).

Those usable as the data base include, for example, GenBank, EMBL, and DDBJ published, for example, from Los Alamos National Institute in the United States, Institute of European Molecular Biology, and National Institute of Genetics (Japan). Those commercially available and useable as the program for homology search include, for example, commercially available DNA analysis softwares, such as DNASIS (Hitachi Software Engineering Co.,Ltd.) and GENETYX (SDC Software Development). The following methods are also available. That is, a computer terminal is connected with the host computer of National Institute of Genetics to perform analysis. Alternatively, a personal computer is connected on Internet with NCBI (National Center for Biotechnology Information) to utilize (http://www.ncbi.nlm.nih.gov/BLAST/) BLAST (Basic Local Alignment Search Tool) so that high speed homology search is performed.

The homology search is performed, for example, in accordance with the following algorithm. When the homology search is performed for a nucleotide sequence, homology comparison is advanced while shifting the nucleotide sequence to be investigated by every one nucleotide with respect to individual gene sequences included in the data base. When six or more continuous nucleotides are coincident, the homology score is counted and calculated in accordance with a homology score table (see, for example, M. Dayhoff, *Atlas of Protein Sequence and Structure*, vol. 5 (1978)). The system is set so that those having a score not less than a certain value are picked up as candidates which have homology. Further, the gap may be introduced into the sequence to be investigated or into the gene sequence included in the data base to make optimization so that the score is maximized.

When the homology search is performed for an amino acid sequence, a nucleotide sequence to be investigated is converted into amino acids concerning all six frames including those of a complementary chain. The investigation may be performed in the same manner as performed for the nucleotide. Specifically, it is possible to use blastx of BLAST described above. As for detailed techniques and conditions for the search, reference may be made to *DDBJ News Letter*, No. 15 (February 1995).

<4> Isolation of cDNA Clone of Cotton Slant Cellulose Synthase

The clone obtained as described above is not necessarily contain the entire nucleotide sequence of the gene. In such a case, the clone is used as a probe to perform screening by means of plaque hybridization. Thus, it is possible to obtain a clone containing a full length gene frou the library. A specified method may be carried out with reference to *Molecular Cloning*, second edition (Maniatis et al., Cold Spring Harbour Laboratory) 12.30 to 12.40.

When obtained cDNA is deficient in 5'-portion, the 5'-portion can be obtained as well by synthesizing primers so th at the cDNA sequence may be elongated toward the 5'-terminal, and performing RT-PCR by using mRNA as a template.

As demonstrated in Examples described later on, the DNA of the present invention has been obtained as those having homology to the known bacterial cellulose synthase gene. The DNA further codes for an amino acid sequence GlnXXXXXXArgTrp (SEQ ID NO: 12) which is considered to form a UDP-glucose binding domain, having high homology in the vicinity thereof.

The nucleotide sequences of DNA of the present invention obtained as described above and the amino acid sequences deduced from the nucleotide sequences are shown in SEQ ID NOs: 1 to 10 in Sequence Listing. SEQ ID Nos: 1 and 3 show nucleotide sequences of PcsA1 and PcsA2 respectively. SEQ ID NOs: 2 and 4 show amino acid sequences de duced from the nucleotide sequences of PcsA1 and PcsA2 respectively.

SEQ ID NOs: 5 and 6 show a nucleotide sequence of a clone (PcsA3-682) containing 3'-side region of PcsA3 and an amino acid sequence deduced from the nucleotide sequence respectively. SEQ ID NOs: 7 and 8 show a nucleotide sequence of a 5'-portion (PcsA3-5') of another clone containing 5'-side region of PcsA3 and an amino acid sequence deduced from the nucleotide sequence respectively. SEQ ID NOs: 9 and 10 show a nucleotide sequence of 3'-portion (PcsA3-3') of the clone and an amino acid sequence deduced from the nucleotide sequence respectively (see FIG. 1). That is, SEQ ID NO: 5 corresponds to the 3'-side region of PcsA3, SEQ ID NO: 7 corresponds to the 5'-side region of PcsA3, and SEQ ID NO: 9 corresponds to internal region of PcsA3. The overlapping portion of PcsA3-682 is different from that of PcsA3-3' in 9 nucleotides in the nucleotide sequence and 1 amino acid in the amino acid sequence. FIGS. 3 and 4 show the comparison between the nucleotide sequences of PcsA3-682 and PcsA3-3'. SEQ ID NO: 11 shows a combination of the amino acid sequences encoded by PcsA3-682 and PcsA3-3'.

The sequence of GlnXXXXXXArgTrp (SEQ ID NO: 12) corresponds to amino acid numbers 710 to 714 in SEQ ID NO: 2 for PcsA1, amino acid numbers 778 to 782 in SEQ ID NO: 4 for PcsA2, and amino acid numbers 356 to 360 in SEQ ID NO: 6 for PcsA3.

PcsA1 is different from CelA1 reported by Pear et al. (*Proceeding of National Academy of Science, USA* (1996), 93, 12637–12642) in nucleotide sequence by 28 nucleotides. As a result, the former is different from the latter in amino acid sequence encoded thereby by 10 amino acid residues. In general, the sugar chain specificity and the substrate specificity of the sugar chain transferase are extremely changed by point mutation of the nucleotide of DNA (Yamamoto and Hakomori, *The Journal of Biological Chemistry* (1990) 265, 19257–19262). Therefore, it is unclear whether or not CelA1 codes for a protein having the cellulose synthase activity. Incidentally, the 48th Arg, the 56th Ser, the 81st Asn, the 104th Ala, the 110th Ser, the 247th Asp, the 376th Asp, the 386th Ser, the 409th Arg, and the 649th Ser in the amino acid sequence encoded by CelA1 correspond to Gln, Ile, Ser, Thr, Pro, Asn, Glu, Pro, His, and Gly in PcsA1 respectively.

PcsA2 of the present invention contains the same sequence as that of CelA2 reported by Pear et al. However, CelA2 has an incomplete length, and it does not contain the entire coding region. CelA2 corresponds to nucleotide numbers of 1083 to 3311 in the nucleotide sequence of PcsA2 shown in SEQ ID NO: 3.

Any of the amino acid sequences shown in SEQ ID NOs: 2, 4, 6, 8, 10, and 11 is a novel sequence. All genes having nucleotide sequences coding for the amino acid sequences are included in the present invention.

The amino acid sequences described above may include deletion, substitution, insertion, and/or addition of one or more amino acid residues provided that the characteristic of the gene of the present invention is not substantially affected. The deletion, substitution, insertion, and/or addition of one or more amino acid residues as described above is obtainable by modifying the DNA's coding for the amino acid sequences shown in SEQ ID NOs: 2, 4, 6, 8, 10, and 11 randomly in accordance with the ordinary mutation treatment or intentionally in accordance with the site-directed mutagenesis method. As described above, in general, the sugar chain specificity and the substrate specificity of the sugar chain transferase are extremely changed by point mutation of the nucleotide of DNA. Therefore, DNA coding for a protein having the cellulose synthase activity is selected from the modified DNA's. The cellulose synthase activity can be measured, for example, by means of the method described by T. Hayashi: Measuring-β-glucan deposition in Dlant cell walls, in *Modern Methods of Plant Analysis: Plant Fibers*, eds. H. F. Linskens and J. F. Jackson, Springer-Verlag, 10: 138–160 (1989).

Those harboring proteins or genes partially different from the sequences shown in Sequence Listing may exist depending on, for example, the variety of cotton plant or natural mutation. However, such genes are also included in the gene of the present invention. Such a gene may be obtained as DNA which is hybridizable under the stringent condition with all or a part of the coding region of the nucleotide sequence shown in SEQ ID NO: 1, 3, 5, 7, or 9. The "stringent condition" referred to herein indicates a condition under which a so-called specific hybrid is formed, and non-specific hybrid is not formed. It is difficult to definitely express such a condition by using a numerical value. However, for example, the stringent condition is exemplified by a condition under which nucleic acids having high homology, for example, DNA's having homology of not less than 80% undergo hybridization with each other, and nucleic acids having homology lower than the above do not undergo hybridization with each other.

<5> Utilization of Gene of the Present Invention

The DNA of the present invention makes it possible to control the cellulose synthesis in prokaryotic cells such as acetobacterium and/or eukaryotic cells such as yeasts belonging to, for example, the genus Saccharomyces, cells of plant such as cotton plant, and cultured cells of mammals and the like.

Specifically, the cellulose synthesis in the cells as described above can be facilitated, for example, by connecting a promoter to an upstream region of the DNA of the present invention, inserting an obtained fragment into an appropriate vector to construct a recombinant vector, and introducing the vector into the cells. Alternatively, the cellulose synthesis in the cells can be suppressed by introducing an antisense gene of the DNA of the present invention into the cells.

The promoter and the vector may be selected from those ordinarily utilized to express heterogeneous genes, and the method ordinarily employed to express heterogeneous genes may be used as the transformation method. Specifically, in the case of yeast, it is possible to use a protein-expressing kit produced by Invitrogen, i.e., Pichia Expression Kit, and a vector pPIC9 contained in this kit. For example, COS7 cells may be used as mammalian cultured cells, and a vector CDM8 may be used therefor.

The present invention provides the DNA coding for cellulose synthase. The DNA provides a new method for controlling cellulose production by incorporating the DNA into prokaryotic cells and eukaryotic cells.

BRIEF DESCRIPTION OF THE DRAWINGS

FIG. 3 shows comparison between sequences of PcsA3-682 and PcsA3-3' (former half).

FIG. 4 shows comparison between sequences of PcsA3-682 and PcsA3-3' (latter half). ":" indicates coincident nucleotides, and "*" indicates non-coincident nucleotides.

BEST MODE FOR CARRYING OUT THE INVENTION

Figures 1, 2:
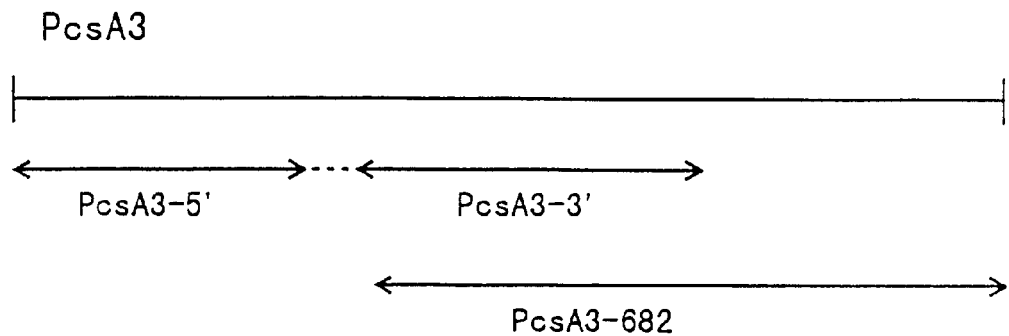
FIG. 1 shows a relationship between two clones of PcsA3 as an embodiment of the DNA of the present invention. Regions interposed between arrows indicate regions for which nucleotide sequences have been determined. A dotted line indicates a region for which no nucleotide sequence has been determined.
FIG. 2 shows a structure of EcoRI adapter.

Examples of the present invention will be explained below.

<1> Preparation of Total RNA from Cotton Plant

Cotton plant (*Gossypium hirsutum* L.) Coker 312 was used as a material. Fiber cells on 16 to 18 days post anthesis were collected in liquid nitrogen. The cotton plant fiber cells in an amount of 75 g were sufficiently ground in a mortar while being frozen with liquid nitrogen. Powdered fiber was transferred to a centrifuge tube equipped with a cap, to which 375 mg of DTT as a powder was added, followed by addition of 200 ml of XT buffer (obtained by adjusting 0.2 M sodium borate containing 30 mM EDTA and 1% SDS to be pH 9.0, and then applying a diethylpyrocarbonate treatment, followed by autoclaving to obtain a solution to which vanadylribonucleoside was added to give a concentration of 10 mM) having been heated to 90 to 95° C. An obtained solution was sufficiently agitated.

The solution was added with 100 mg of protease K, and it was agitated again. The solution was incubated at 40° C. for 2 hours, and then it was added with 16 ml of 2 M KCl. The solution was sufficiently agitated again, and it was left to stationarily stand in ice for 1 hour, followed by centrifugation for 20 minutes (4 ° C.) at 12,000 g by using a high speed refrigerated centrifuge.

An obtained supernatant was filtrated, and floating matters were removed. The solution was transferred to a measuring cylinder to measure the volume. The solution was transferred to another centrifuge tube, to which lithium chloride was added in an amount of 85 mg per 1 ml of the extract solution to give a final concentration of 2 M. The solution was left to stationarily stand at 4° C. overnight, and then precipitated RNA was separated by centrifugation for 20 minutes at 12,000 g. An obtained precipitate of RNA was washed and precipitated twice with cooled 2 M lithium chloride.

The obtained RNA was dissolved in 10 mM Tris buffer (pH 7.5) to give a concentration of about 2 mg/ml, to which 5 M potassium acetate was added to give a concentration of 200 mM. Ethanol was added thereto to give a concentration of 70%, followed by cooling at −80° C. for 10 minutes. Centrifugation was performed at 4° C. for 10 minutes at 15,000 rpm, and then an obtained precipitate was suspended in an appropriate amount of sterilized water to give an RNA sample. As a result of quantitative measurement for the RNA sample, total RNA was obtained in an amount of 2 mg.

<2> Purification of mRNA mRNA was purified as a poly(A)$^+$ RNA fraction from the total RNA obtained as described above. Purification was performed by using Oligotex-dT30 <Super> (purchased from Toyobo) as oligo(dT)-immobilized latex for poly(A)$^+$ RNA purification.

Elution buffer (10 mM Tris-HCl (pH 7.5), 1 mM EDTA, 0.1% SDS) was added to a solution containing 1 mg of the total RNA to give a total volume of 1 ml, to which 1 ml of Oligotex-dT30 <Super> was added, followed by heating at 65° C. for 5 minutes and quick cooling on ice for 3 minutes. The obtained solution was added with 0.2 ml of 5 M NaCl, and it was incubated at 37° C. for 10 minutes, followed by centrifugation at 15,000 rpm for 3 minutes. After that, a supernatant was carefully removed.

An obtained pellet was suspended in 2.5 ml of Washing Buffer (10 mM Tris-HCl (pH 7.5), 1 mM EDTA, 0.5 M NaCl, 0.1% SDS), and the suspension was centrifuged at 15,000 rpm for 3 minutes. After that, a supernatant was carefully removed. An obtained pellet was suspended in 1 ml of TE Buffer, and then it was heated at 65° C. 5 minutes. The suspension was quickly cooled on ice for 3 minutes, and then it was centrifuged at 15,000 rpm for 3 minutes to recover poly(A)$^+$ mRNA contained in an obtained supernatant.

Thus, the poly(A)$^+$ mRNA in an amount of about 10 μg was obtained from 1 mg of the total RNA. An aliquot of 5 μg thereof was used to prepare a cDNA library.

<3> Preparation of cDNA Library (1) Synthesis of cDNA

The mRNA obtained as described above was used as a template to synthesis cDNA by using a λZAP cDNA synthesis kit produced by Stratagene. The following solution was prepared and mixed in a tube.

5.0 μl 10×1st Strand Buffer (buffer for reverse transcription reaction);

3.0 μl 10 mM 1st Strand Methyl Nucleotide Mix (5-methyl dCTP, dATP, dGTP, dTTP mixture);

2.0 μl Linker-Primer (linker and primer);

H$_2$O (adjusted to give a total volume of 50 μl);

1.0 μl RNase Block II (RNase inhibitor).

The respective components described above were contents of the kit. Linker-Primer had a sequence as shown in SEQ ID NO: 13. Methylated nucleotide was used because it was intended not to allow cDNA to be digested by the restriction enzyme reaction performed later on. The reaction solution was agitated well, and then 5.0 μg of poly(A)$^+$ mRNA was added thereto, followed by being left to stand at room temperature for 10 minutes. Further, 2.5 μl of M-MuLV RTase (reverse transcriptase) was added (at this time, the total volume was 50 μl). The reaction solution was gently mixed, followed by centrifugation under a mild condition to allow the reaction solution to fall to the bottom of the tube. The reaction was performed at 37° C. for 60 minutes.

Next, the following solution was prepared and mixed in the tube in a certain order.

45.0 μl reaction solution containing cDNA primary chain;

40.0 μl 10×2nd Strand Buffer (buffer for polymerase reaction);

6.0 μl 2nd Strand Nucleotide Mixture (A, G, C, T mixture);

302.0 μl H$_2$O.

The following solution was further added. However, in order to allow RNase and DNA polymerase to simultaneously act, enzyme solutions were allowed to adhere to the wall of the tube. After that, a vortex treatment was promptly performed, and the reaction solutions were allowed to fall to the bottom of the tube by means of centrifugation to perform a reaction for synthesizing cDNA second strand at 16° C. for 150 minutes.

0.8 μl RNase H (RNA-degrading enzyme);

7.5 μl DNA polymerase I (10.0 u/μl).

The reaction solution was added with 400 μl of a mixed solution of phenol: chloroform (1:1). Agitation was performed well, followed by centrifugation at room temperature for 2 minutes. An obtained supernatant was added with 400 μl of phenol: chloroform again, which was subjected to a vortex treatment and centrifugation at room temperature for 2 minutes. An obtained supernatant was added with the following solution to precipitate cDNA.

33.3 µl 3 M sodium acetate solution;

867.0 µl 100% ethanol.

The obtained solution was left to stand at −20° C. overnight, and it was centrifuged at room temperature for 60 minutes. After that, washing was gently performed with 80% ethanol, followed by centrifugation for 2 minutes. A supernatant was removed. An obtained pellet was dried, and it was dissolved in 43.5 µl of sterilized water. An aliquot (39.0 µl) was added with the following solution to blunt-end cDNA terminals. 5.0 µl 10×T4 DNA Polymerase Buffer (buffer for T4 polymerase reaction);

2.5 µl 2.5 mM dNTP Mix (A, G, C, T mixture);

3.5 µl T4 DNA polymerase (2.9 u/µl).

The reaction was performed at 37° C. for 30 minutes, to which 50 µl of distilled water was added, and then 100 µl of phenol: chloroform was added thereto, followed by a vortex treatment and centrifugation for 2 minutes. An obtained supernatant was added with 100 µl of chloroform, which was subjected to a vortex treatment, followed by centrifugation for 2 minutes. The supernatant was added with the following solution to precipitate cDNA.

7.0 µl 3 M sodium acetate solution;

226 µl 100% ethanol.

The solution was left to stand on ice for 30 minutes or more, and it was centrifuged at 4° C. for 60 minutes. An obtained precipitate was washed with 150 µl of 80% ethanol, followed by centrifugation for 2 minutes and drying. The cDNA pellet was dissolved in 7.0 µl of EcoRI Adaptor solution, to which the following solution was added to ligate the EcoRI adapter to both ends of the cDNA. Sequences of respective strands of the EcoRI adapter are shown in SEQ ID NO: 14 and FIG. 2.

1.0 µl 10×Ligation Buffer (buffer for ligase reaction);

1.0 µl 10 mM ATP;

1.0 µl T4 DNA ligase.

The reaction solution was centrifuged under a mild condition, and it was left to stand at 4° C. overnight or more. The solution was treated at 70° C. for 30 minutes, and then it was centrifuged under a mild condition, followed by being left to stand at room temperature for 5 minutes. The reaction solution was added with the following solution to phosphorylate 5'-terminals of the EcoRI adapter.

1.0 µl 10×Ligation Buffer (buffer for ligase reaction);

2.0 µl 10 mM ATP;

6.0 µl H$_2$O;

1.0µl T4 polynucleotide kinase (10.0 u/µl).

The reaction was performed at 37° C. for 30 minutes, followed by a treatment at 70° C. for 30 minutes. The solution was centrifuged under a mild condition, and it was left to stand at room temperature for 5 minutes. The following solution was further added thereto to perform a reaction at 37° C. for 90 minutes so that the XhoI site introduced by Linker-Primer was digested with XhoI, followed by being left to stand at room temperature to perform cooling.

28.0 µl XhoI Buffer;

3.0 µl XhoI (45 u/µl).

The reaction solution was added with 5.0 µl of 10×STE (10 mM Tris-HCl (pH 8.0), 100 mM NaCl, 1 mM EDTA), which was added into a centrifuge column for removing short fragments (Sephacryl Spin Column) to perform centrifugation at 600 g for 2 minutes to obtain an eluent which was designated as Fraction 1. This operation was further repeated three times to obtain Fractions 2, 3, and 4 respectively. Fractions 3 and 4 were combined, to which phenol: chloroform (1:1) was added and agitated well, followed by centrifugation at room temperature for 2 minutes. An obtained supernatant was added with an equal amount of chloroform, and an obtained mixture was agitated well. The mixture was centrifuged at room temperature for 2 minutes to obtain a supernatant to which a two-fold amount of 100% ethanol was added, followed by being left to stand at −20° C. overnight. The solution was centrifuged at 4° C. for 60 minutes, followed by washing with an equal amount of 80% ethanol. The solution was centrifuged at 4° C. for 60 minutes to obtain a cDNA pellet which was suspended in 10 µl of sterilized water.

(2) Preparation of cDNA Library

The double strand cDNA obtained as described above was ligated with λ phage expression vector to prepare a recombinant vector. The following solution was prepared and mixed in a tube to perform a reaction at 12° C. overnight, followed by being left to stand at room temperature for 2 hours to ligate cDNA with the vector.

2.5 µl cDNA solution;

0.5 µl 10×Ligation Buffer;

0.5 µl 10 mM ATP;

1.0 µl λZAP vector DNA (1 µg/µl);

0.5 µl T4 DNA ligase (4 Weiss u/µl).

(3) Packaging of Phase DNA into Phase Particles

The phage vector containing the cDNA was packaged into phage particles by using an in vitro packaging kit (Gigapack II Gold packaging extract: produced by Stratagene). The recombinant phage solution was added to Freeze/Thaw extract immediately after dissolution, and the solution was placed on ice, to which 15 µl of Sonic extract was added to perform mixing well by pipetting. The reaction solution was centrifuged under a mild condition, and it was left to stand at room temperature (22° C.) for 2 hours. The reaction solution was added with 500 µl of Phage Dilution Buffer, to which 20 µl of chloroform was further added, followed by mixing. In order to measure the titer of the library, an aliquot (2 µl) of 500 µl of the aqueous phase was diluted in a ratio of 1:10 with 18 µl of SM buffer (5.8 g of NaCl, 2 g of MgSo$_4$·7H$_2$O, 50 ml of 1 M Tris-HCl (pH 7.5), and 5 ml of 2% gelatin in 1 L). The diluted solution (1 µl) and the phage stock solution (1 µl) were plated respectively together with 200 µl of a culture solution of *Escherichia coli* PLK-F' strain having been cultivated to arrive at a value of OD$_{600}$ of 0.5. That is, *Escherichia coli* PLK-F' strain was mixed with the phage solution to perform cultivation at 37° C. for 15 minutes. The obtained culture was added to 2 to 3 ml of top agar (48° C.), which was immediately overlaid on NZY agar plate having been warmed at 37° C. Cultivation was performed overnight at 37° C., and appeared plaques were counted to calculate the titer. As a result, the titer was 1.2×10$^6$ pfu/ml.

(4) Amplification of Library

A centrifuge tube was added with the packaging solution containing about 50,000 recombinant bacteriophages and 600 µl of a culture solution of *Escherichia coli* PLK-F' strain having been cultivated to have a value of OD$_{600}$ of 0.5, followed by cultivation at 37° C. for 15 minutes. The culture solution was added with 6.5 ml of top agar having been maintained at 48° C. after dissolution, which was overlaid on 150 mm NZY plate having been warmed at about 37° C., followed by cultivation at 37° C. for 5 to 8 hours. The respective plates were added with 10 ml of SM Buffer to perform cultivation at 4° C. overnight with gentle shaking. SM Buffer in the respective plates was collected in a sterilized polypropylene tube. The respective plates were rinsed with 2 ml of SM Buffer, and the rinsing solutions were collected in the same tube. Chloroform in an amount corresponding to 5% of the total amount was added and mixed, followed by being left to stand at room temperature for 15 minutes. Bacterial cells were removed by centrifugation at 4,000 g for 5 minutes. An obtained supernatant was added with chloroform in an amount corresponding to 0.3% of the total amount, and it was stored at 4° C. The titer of the library amplified as described above was measured in the same manner as described above. As a result, the titer was $2.3 \times 10^9$ pfu/ml.

(5) Excision of Plasmid from Phase DNA

In vivo excision of the plasmid portion from the recombinant phage DNA was performed. The following solution was mixed in 50 ml of a conical tube to cause infection at 37° C. for 15 minutes:

culture solution of *Escherichia coli* XL1-Blue ($OD_{600}$ =0.1) 200 µl;

phage solution after amplification 200 µl ($<1 \times 10^5$ phage particles);

helper phage R408 1 µl ($<1 \times 10^6$ pfu/ml).

The mixed solution was added with 5 ml of 2×YT medium to perform cultivation at 37° C. for 3 hours with shaking. A heat treatment was applied thereto at 70° C. for 20 minutes, followed by centrifugation at 4,000 g for 5 minutes. An obtained supernatant was decanted and transferred to a sterilized tube. Centrifugation was performed to obtain a supernatant which was diluted 100 times to obtain a solution. An aliquot (20 µl) of the solution was mixed with 200 µl of a culture solution of *Escherichia coli* XL1-Blue having been cultivated to obtain a value of $OD_{600}$ of 1.0 to cause infection at 37° C. for 15 minutes. Aliquots (1 to 100 µl) of the culture solution were plated on LB plates containing ampicillin, followed by cultivation at 37° C. overnight. Appeared colonies were randomly selected. Selected colonies were added with glycerol, and they were stored at −80° C.

(6) Preparation of Plasmid

Plasmids were prepared by using Magic Mini-prep kit produced by Promega. The culture fluid of *Escherichia coli* harboring the plasmid having been stored at −80° C. was inoculated into 5 ml of 2×YT medium, followed by cultivation at 37° C. overnight. Centrifugation was performed for 5 minutes (4,000 rpm, 4° C.), and a supernatant was removed by decantation. An obtained a bacterial cell pellet was added with 1 ml of TE buffer, followed by a vortex treatment. An obtained bacterial cell suspension was transferred to an Eppendorf tube, followed by centrifugation for 5 minutes (5,000 rpm, 4° C.). A resultant supernatant was removed by decantation.

An obtained bacterial cell pellet was added with 300 µl of Cell Resuspension Solution, and it was sufficiently suspended therein. An obtained suspension was transferred to an Eppendorf tube. The suspension was agitated for 2 minutes with a mixer, to which 300 µl of Cell Lysis Solution was added, followed by agitation until the suspension became transparent. Neutralization Solution (300 µl) was added thereto, and agitation was performed by shaking with the hand, followed by centrifugation for 10 minutes (15,000 rpm).

Only an obtained supernatant was transferred to a new Eppendorf tube (1.5 ml). A suction tube was prepared, to which a cock, a miniature column and a syringe (injector) were connected in this order. A resin in an amount of 1 ml was charged into the syringe. The supernatant was poured into the syringe, and agitation was performed well, followed by suction. Column Washing Solution in an amount of 2 ml was added, and washing was performed while performing suction. Suction was continued for 1 to 2 minutes in order to dry up. The miniature column was removed from the equipment, and it was set in a new Eppendorf tube (1.5 ml). Sterilized water in an amount of 100 µl having been warmed at 65 to 70° C. was poured into the miniature column, and the column and the Eppendorf tube were centrifuged together for 1 minute (5,000 rpm). An eluted solution was transferred to an Eppendorf tube, to which 5 µl of 3 M sodium acetate aqueous solution was added, and 250 µl of cold ethanol was added thereto. The solution was centrifuged (15,000 rpm, 25 minutes), and a supernatant was discarded. An obtained precipitate was added with 1 ml of 70% ethanol, followed by centrifugation again (15,000 rpm, 3 minutes). Ethanol was completely removed, and the tube was vacuum-dried in a desiccator. The precipitate was sufficiently dissolved in 20 µl of sterilized water, and an obtained solution was stored at −20° C. An aliquot (1 µl) of the solution was dispensed, and it was subjected to electrophoresis together with volume markers to quantitatively determine the plasmid DNA.

<4> Determination of Nucleotide Sequence of cDNA and Homology Search with Gene Data Base (1) Determination of Nucleotide Sequence of cDNA The nucleotide sequence of cDNA was analyzed by using DNA automatic sequencer 373A produced by Applied Biosystems Inc. (ABI). The sequencing reaction was performed in accordance with an attached manual by using T3 primer based on the use of Dye Primer Cycle Sequencing Kit produced by the same company. The nucleotide sequence was determined for about 750 clones which were randomly selected.

(2) Homology Search

Partial sequences of about 750 clones were searched with a computer using BlastX. As a result, three clones appeared to be homologues of bacterial cellulose synthase subunit. Therefore, it was tried to isolate full length clones.

<5> Isolation of Full Length Clones (1) 5'-RACE

As a result of the homology search, the obtained homologue clones were found to be partial length clones. Therefore, primers were synthesized to make elongation toward the 5' upstream so that RT-PCR was performed by using mRNA as a template.

(1-a) Synthesis of First-strand DNA

The following solution was prepared and mixed in a tube.

0.5 µl 10 µmol gene-specific primer 1;

1 µg total RNA;

DEPC-treated $H_2O$ (adjusted to give a total amount of 9 µl).

The following oligonucleotides were used as the gene-specific primer 1. That is, an oligonucleotide having a nucleotide sequence shown in SEQ ID NO: 15 was used for PcsA1. An oligonucleotide having a nucleotide sequence shown in SEQ ID NO: 16 was used for PcsA2. An oligonucleotide having a nucleotide sequence shown in SEQ ID NO: 17 was used for PcsA3.

The reaction solution was gently mixed, and then it was centrifuged under a mild condition to allow the reaction solution to fall to the bottom of the tube. The solution was left to stand at 70° C. for 10 minutes, followed by immediate cooling on ice.

Next, the following solution was prepared and mixed in the tube.

5×RT Buffer 5 µl;

25 mM MgCl$_2$ 2.5 µl;

2 mM dNTP mix 5 µl;

0.1 M DTT 2.5 µl;

H$_2$O (added to give a total amount of 24 µl).

The solution was gently agitated, and then it was centrifuged under a mild condition to allow the reaction solution to fall to the bottom of the tube, followed by being left to stand at 42° C. for 1 minute. The solution was added with 1 µl of SuperScriptII RT (reverse transcriptase, GIBCO BRL), and it was gently mixed. After that, the reaction was performed at 42° C. for 50 minutes. Subsequently, the reaction solution was left to stand at 70° C. for 15 minutes to stop the reaction. Centrifugation was performed under a mild condition to allow the reaction solution to fall to the bottom of the tube, followed by being left to stand at 37° C. RNase H (produced by Toyobo) in an amount of 1 µl was added thereto to perform a reaction at 37° C. for 30 minutes.

Subsequently, in order to remove excessive primers and nucleotides contained in the reaction solution, gel filtration was performed by using a purification column produced by Boehringer, Quick Spin Columns. At first, the tip of the column was removed, followed by centrifugation at 1,100×g for 2 minutes to discard the buffer. The reaction solution was introduced into the central area of the column, followed by centrifugation at 1,100×g for 4 minutes to recover the solution.

(1-b) Poly(dC) Tailing

An aliquot (5 µl) was dispensed from the obtained solution, to which the following solution was added.

5 µl 5×CoCl$_2$ Buffer;

2.5 µl 2 mM dCTP;

H$_2$O (adjusted to give a total amount of 24 µl).

The reaction solution was mixed well, and it was left to stand at 94° C. for 3 minutes. Centrifugation was performed under a mild condition to allow the reaction solution to fall to the bottom of the tube, followed by being left to stand on ice. Terminal transferase TdT (produced by Toyobo) was added thereto in an amount of 1 µl, followed by mixing under a mild condition to perform a reaction at 37° C. for 10 minutes. Subsequently, the reaction solution was left to stand at 65° C. for 10 minutes to stop the reaction.

(1-c) PCR Reaction

An aliquot (2.5 µl) was dispensed from the reaction solution, to which the following solution was added.

2.5 µl 10×PCR Buffer;

2.5 µl 2 mM dNTP mix;

0.5 µl Gene-specific primer 2;

0.5µl Abridged Anchor Primer (GIBCO BRL);

0.5 µl Advantage Klentaq Polymerase Mix (Clontech);

H$_2$O (adjusted to give a total amount of 25 µl).

The following oligonucleotides were used as Gene-specific primer 2. That is, an oligonucleotide having a nucleotide sequence shown in SEQ ID NO: 18 was used for PcsA1. An oligonucleotide having a nucleotide sequence shown in SEQ ID NO: 19 was used for PcsA2. An oligonucleotide having a nucleotide sequence shown in SEQ ID NO: 20 was used for PcsA3.

The solution was introduced into a 0.2 ml tube to perform the PCR reaction under the following condition.

| PAD | 94° C. | 90 seconds |
|---|---|---|
| 30 cycles | 94° C. | 30 seconds |
| | 60 to 68° C. | 30 to 60 seconds |
| | 68° C. | 180 seconds |
| Final | 68° C. | 7 minutes |
| Hold | 4° C. | |

The reaction solution was subjected to agarose gel electrophoresis to extract, from the gel, DNA's corresponding to portions having the largest size (about 1.8 K for PcsA1, about 2 K for PcsA2, and about 2.2 K for PcsA3). GENO-BIND produced by CLONTECH was used for the extraction, and the procedure was carried out in accordance with its protocol. The DNA thus obtained was subjected to Poly(dC)tailing, which was used as a template to perform the PCR reaction. The condition and the composition of the reaction solution were the same as those described above.

(2) Cloning (2-a) 5'-RACE TA Cloning

Starting from the obtained PCR reaction solution, cloning was performed by using TA Cloning Kit produced by Invitrogen in accordance with its protocol.

The following solution was added to an aliquot (1.5 µl) of the PCR reaction solution obtained as described above.

0.5 µl 10×Ligation Buffer;

1 µl pCRII vector;

0.5 µl T4 DNA Ligase;

1.5 µl dH$_2$O.

The reaction was performed at 14° C. overnight. An aliquot (2 µl) of the reaction solution was added to 25 µl of *Escherichia coli* competent cell (JM109) preparation, followed by being left to stand for 30 minutes on ice. After that, heat shock was applied at 42° C. for 30 seconds. The solution was stationarily left to stand on ice for 2 minutes, to which 450 µl of SOB medium was thereafter added to perform cultivation at 37° C. for 1 hour with shaking at 200 rpm. The culture was spread over Amp/Xgal/IPTG plate, followed by incubation at 37° C. overnight. The plasmid was extracted from obtained colonies in accordance with the method as described above.

(2-b) Cloning of Complete Length cDNA

The procedure was carried out by using DNA Sequencer 377 produced by ABI in accordance with its protocol. The sequencing reaction was performed by using M13 primer and synthetic oligomer as primers, based on the use of Dye Terminater Cycle Sequencing Kit produced by the same company. As a result of the sequencing, as for PcsA3, it was revealed that another clone also belonging to the group of PcsA3 but having a slightly different sequence (one position for amino acid) was isolated (see FIGS. 3 and 4). A nucleotide sequence of a clone (PcsA3-682) containing the 3'-side region of PcsA3 and an amino acid sequence deduced from this nucleotide sequence are shown in SEQ ID NOs: 5 and 6. A nucleotide sequence of a 5'-portion (PcsA3-5') of another clone containing the 5'-side region of PcsA3 and an amino acid sequence deduced from this nucleotide sequence are shown in SEQ ID NOs: 7 and 8. A nucleotide sequence of a 3'-portion (PcsA3-3') of the clone and an amino acid sequence deduced from this nucleotide sequence are shown in SEQ ID NOs: 9 and 10.

As for PcsA1 and PcsA2, primers for 5'-terminal and 3'-terminal of a region containing ORF were synthesized on the basis of the obtained sequences to perform the PCR reaction. Thus, complete length clones were isolated by means of TA cloning. The condition and the composition of the reaction solution were the same as those described above.

Oligonucleotides shown in SEQ ID NO: 21 (5'-terminal) and SEQ ID NO: 22 (3'-terminal) were used as the primers for PcsA1. Oligonucleotides shown in SEQ ID NO: 23 (5'-terminal) and SEQ ID NO: 24 (3'-terminal) were used as the primers for PcsA2. Results are shown in SEQ ID NOs: 1 to 4.

What is claimed is:

1. A DNA coding for a protein having cellulose synthase activity and comprising the amino acid sequence shown in SEQ ID NO: 2.

2. The DNA according to claim 1, wherein the DNA is the polynucleotide sequence corresponding to nucleotides 77 to 3001 in SEQ ID NO: 1.

3. A recombinant vector comprising the DNA of claim 1.

4. A transformed cell transformed with the DNA of claim 1.

5. A method for controlling cellulose synthesis in a cell, comprising the steps of introducing the DNA of claim 1, or mRNA fully corresponding thereto, into the cell, and expressing the protein encoded by said DNA or corresponding mRNA.

6. A DNA coding for a protein having cellulose synthase activity and comprising the amino acid sequence shown in SEQ ID NO: 4, or coding for a fragment of said protein having cellulose synthase activity.

7. The DNA according to claim 6, wherein the DNA is the polynucleotide sequence corresponding to nucleotides 23 to 3142 in SEQ ID NO: 3.

8. A recombinant vector comprising the DNA of claim 6.

9. A transformed cell transformed with the DNA of claim 6.

10. A method for controlling cellulose synthesis in a cell, comprising the steps of introducing the DNA of claim 6, or mRNA fully corresponding thereto, into the cell, and expressing the protein encoded by said DNA or corresponding mRNA.

11. A DNA coding for a protein having cellulose synthase activity and comprising both the amino acid sequence shown in SEQ ID NO: 8 and the amino acid sequence shown in SEQ ID NO: 11, or coding for a fragment of said protein having cellulose synthase activity.

12. The DNA according to claim 11, wherein the DNA comprises the polynucleotide sequence corresponding to nucleotides 24 to 1086 in SEQ ID NO: 7 and the polynucleotide sequence corresponding nucleotide 1 to 1857 in SEQ ID NO: 5.

13. A recombinant vector comprising the DNA of claim 11.

14. A transformed cell transformed with the DNA of claim 11.

15. A method for controlling cellulose synthesis in a cell, comprising the steps of introducing the DNA of claim 11, or mRNA fully corresponding thereto, into the cell, and expressing the protein encoded by said DNA or corresponding mRNA.

* * * * *